(12) United States Patent
Starck et al.

(10) Patent No.: US 7,645,887 B2
(45) Date of Patent: Jan. 12, 2010

(54) INDOLONE-ACETAMIDE DERIVATIVES, PROCESSES FOR PREPARING THEM AND THEIR USES

(75) Inventors: Jean-Philippe Starck, Gougenheim (FR); Benoît Kenda, Emines (BE)

(73) Assignee: UCB Pharma, S.A., Brussels (BE)

( * ) Notice: Subject to any disclaimer, the term of this patent is extended or adjusted under 35 U.S.C. 154(b) by 407 days.

(21) Appl. No.: 10/550,667

(22) PCT Filed: Mar. 16, 2004

(86) PCT No.: PCT/EP2004/002691

§ 371 (c)(1), (2), (4) Date: Jun. 28, 2006

(87) PCT Pub. No.: WO2004/082658

PCT Pub. Date: Oct. 14, 2004

(65) Prior Publication Data

US 2007/0043038 A1 Feb. 22, 2007

(30) Foreign Application Priority Data

Mar. 31, 2003 (EP) .................................. 03007214

(51) Int. Cl.
C07D 209/34 (2006.01)
A61K 31/4015 (2006.01)
(52) U.S. Cl. ...................... 548/486; 514/418
(58) Field of Classification Search .................. 548/486
See application file for complete search history.

(56) References Cited

U.S. PATENT DOCUMENTS

| 4,624,963 | A | 11/1986 | Kruse et al. |
| 7,129,250 | B2 | 10/2006 | Jaquith et al. |
| 7,202,251 | B2 * | 4/2007 | Bell et al. .................. 514/256 |
| 2009/0012147 | A1 | 1/2009 | Kenda et al. |

FOREIGN PATENT DOCUMENTS

| EP | 0 022 317 A1 | 1/1981 |
| EP | 0 445 781 A1 | 9/1991 |
| EP | 0610553 A1 | 8/1994 |
| JP | 01095766 | 4/1989 |
| SU | 841 264 A1 | 11/1995 |
| WO | 94/29272 A1 | 12/1994 |
| WO | 98/01428 A1 | 1/1998 |
| WO | WO 01/87887 A | 11/2001 |
| WO | WO 2004/087658 A | 10/2004 |

OTHER PUBLICATIONS

RN 132382-5, retrieved from CAPLUS on Jun. 5, 2008.*
RN 39597-63-2, retrieved from CAPLUS on Jun. 5, 2008.*
RN 137641-76-0, retrieved from CAPLUS on Jun. 5, 2008.*
RN 17380-11-9, retrieved from CAPLUS on Jun. 5, 2008.*
RN 680994-79-0, retrieved from CAPLUS on Jun. 5, 2008.*
Silverman, R. Bl The Org. Chem. of Drug Design and Drug Action, Academic Press, Inc. San Diego, (1992) pp. 4-51.*
XP002241130, Database Crossfire Beilstein, Beilstein Institut zur Forderung der Chemischen Wissenschaftern, Franfurt am Main, Germany, Database accession No. BRN:6400176, 3 pages.
Bell, M. et al., J. Med. Chem., 1991, vol. 34, No. 3, pp. 1099-1110.
Hotzel, C. et al., "Design, Synthesis, DNA-Binding and Cytotoxicity Evaluation of New Potential Combilexines", European Journal of Medicinal Chemistry, 2002, vol. 37, No. 5, pp. 367-378.
Chemical Patents Index, Documentation Abstracts Journal, Section Ch, Week 9627, AN 96-266522. XP002241135, (1996).
Patani, George A. Bioisosterism: A rational approach in drug design. Chem. Rev. 96 (1996) 314-3176.
Office Action issued in U.S. Appl. No. 11/572,383, mailed on Feb. 5, 2009.

* cited by examiner

*Primary Examiner*—Rebecca L Anderson
*Assistant Examiner*—Shawquia Young
(74) *Attorney, Agent, or Firm*—McDonnell Boehnen Hulbert & Berghoff LLP

(57) ABSTRACT

The present invention relates to indolone-acetamide derivatives, processes for preparing them, pharmaceutical compositions containing them and their use as for the treatment of epilepsy, epileptogenesis, seizure disorders and convulsion.

11 Claims, No Drawings

INDOLONE-ACETAMIDE DERIVATIVES, PROCESSES FOR PREPARING THEM AND THEIR USES

The present invention concerns indolone-acetamide derivatives, processes for preparing them, pharmaceutical compositions containing them and their use as pharmaceuticals.

European Patent No. 0 162 036 B1 discloses the compound (S)-α-ethyl-2-oxo-1-pyrrolidine acetamide, which is known under the International Nonproprietary Name of levetiracetam.

Levetiracetam, a laevorotatory compound, is disclosed as a protective agent for the treatment and prevention of hypoxic and ischemic type aggressions of the central nervous system. This compound is also effective in the treatment of epilepsy, a therapeutic indication for which it has been demonstrated that its dextrorotatory enantiomer (R)-α-ethyl-2-oxo-1-pyrrolidine acetamide, also known from European Patent No. 0 165 919 B1, completely lacks activity (A. J. GOWER et al, Eur. J. Pharmacol., 222, (1992), 193-203).

Russian patent application SU 841264 discloses 2-(2-oxo-2,3-dihydro-1H-indol-1-yl)acetamide and its anticonvulsant activity.

It has now surprisingly been found that certain indolone-acetamide derivatives demonstrate markedly improved therapeutic properties.

In one aspect the invention therefore provides a compound having the formula I or a pharmaceutically acceptable salt thereof or stereoisomeric forms thereof,

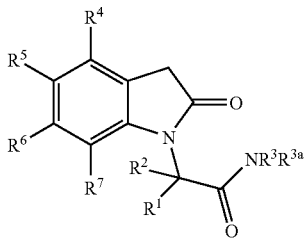

wherein
$R^1$ is hydrogen,
$R^2$ is hydrogen or C1-20-alkyl,
$R^3$ is hydrogen, C1-20-alkyl, C4-8-cycloalkyl, C5-8-cycloalkenyl, aryl, aromatic or non aromatic heterocycle, C1-20-alkoxy, or a group of formula —W—$R^8$,
$R^{3a}$ is hydrogen, C1-20-alkyl or a group of formula:

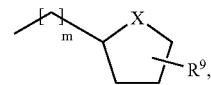

or $NR^3R^{3a}$ is a group of formula

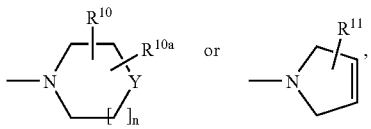

$R^4$ is hydrogen,
$R^5$ is hydrogen; nitro; halogen; azido; cyano; —S—C1-4-alkyl; —SO—C1-4-alkyl; —SO$_2$—C1-4-alkyl; —SONH$_2$; C1-20-alkyl unsubstituted or substituted by halogen; or C1-20-alkoxy unsubstituted or substituted by halogen,
$R^6$ is hydrogen, C1-20-alkyl or halogen,
$R^7$ is hydrogen, C1-20-alkyl or halogen,
W is C1-12-alkylene, —NH— or —NHC(=O)—,
X is O, S or NH,
Y is O, S, —CR$^{12}$R$^{13}$—, —NR$^{14}$— or —C(=O)—,
$R^8$ is aryl or heterocycle,
$R^9$, $R^{10}$, $R^{10a}$ and $R^{11}$ are independently selected from hydrogen, C1-4-alkyl, halogen, hydroxy or methoxycarbonyl, or $R^{10}$ and $R^{10a}$ together form a C3-6-alkylene,
$R^{12}$ is hydrogen, C1-4-alkyl, halogen or hydroxy,
$R^{13}$ is hydrogen,
or CR$^{12}$R$^{13}$ is dioxolanyl,
$R^{14}$ is aryl, heterocycle or a group of formula —V—$R^{15}$,
V is C1-12-alkylene,
$R^{15}$ is aryl or heterocycle,
m is 1 to 4,
n is 0 or 1,
and at least one of $R^5$, $R^6$ or $R^7$ is different from hydrogen when $R^2$ is hydrogen, $R^3$ is H or 2,6-diisopropylphenyl, and $R^{3a}$ is H.

In another aspect the invention provides a compound having the formula I or a pharmaceutically acceptable salt thereof or stereoisomeric forms thereof,

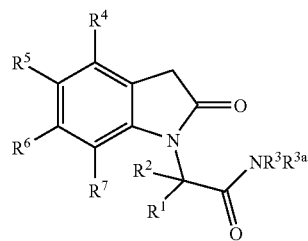

wherein
$R^1$ is hydrogen,
$R^2$ is hydrogen or C1-20-alkyl,
$R^3$ is hydrogen, C1-20-alkyl, C4-8-cycloalkyl, C5-8-cycloalkenyl, aryl, aromatic or non aromatic heterocycle, C1-20-alkoxy, or a group of formula —W—$R^8$,
$R^{3a}$ is hydrogen, C1-20-alkyl or a group of formula:

or $NR^3R^{3a}$ is a group of formula $R^4$ is hydrogen,
$R^5$ is hydrogen; nitro; halogen; C1-20-alkyl unsubstituted or substituted by halogen; or C1-20-alkoxy unsubstituted or substituted by halogen,
$R^6$ is hydrogen, C1-20-alkyl or halogen,
$R^7$ is hydrogen, C1-20-alkyl or halogen,
W is C1-12-alkylene, —NH— or —NHC(=O)—, X is O, S or NH, Y is O, S, —$CR^{12}R^{13}$—, —$NR^{14}$— or —C(=O)—, $R^8$ is aryl or heterocycle, $R^9$, $R^{10}$, $R^{10a}$ and $R^{11}$ are independently selected from hydrogen, C1-4-alkyl, halogen, hydroxy or methoxycarbonyl, or $R^{10}$ and $R^{10a}$ together form a C3-6-alkylene, $R^{12}$ is hydrogen, C1-4-alkyl, halogen or hydroxy, $R^{13}$ is hydrogen, or $CR^{12}R^{13}$ is dioxolanyl, $R^{14}$ is aryl, heterocycle or a group of formula —V—$R^{15}$, V is C1-12-alkylene, $R^{15}$ is aryl or heterocycle, m is 1 to 4, n is 0 or 1, and at least one of $R^5$, $R^6$ or $R^7$ is different from hydrogen when $R^2$ is hydrogen, $R^3$ is H or 2,6-diisopropylphenyl, and $R^{3a}$ is H.

The term "alkyl", as used herein, is defined as including saturated, monovalent hydrocarbon radicals having straight, branched or cyclic moieties or combinations thereof and containing 1-20 carbon atoms, preferably 1-6 carbon atoms and more preferably 1-4 carbon atoms for non-cyclic alkyl and 3-8 carbon atoms for cycloalkyl. Alkyl moieties may optionally be substituted by 1 to 5 substituents independently selected from halogen, hydroxy, alkoxy, alkoxycarbonyl, ester or alkylamino. Preferred alkyl groups are methyl, ethyl, n-propyl, isopropyl, trifluoromethyl, n-butyl, 2-fluoroethyl, 3-hydroxypropyl, 3-hydroxy-2,2-dimethylpropyl, 1-(hydroxymethyl)propyl, 3,3,3-trifluoro-2-hydroxypropyl, 3-ethoxypropyl, 2-ethoxy-2-oxoethyl and 3-(dimethylamino)propyl.

The term "cycloalkyl", as used herein, refers to a monovalent group of 3 to 18 carbon atoms, preferably 4-8 carbon atoms, derived from a saturated cyclic or polycyclic hydrocarbon which may be substituted by any suitable group including but not limited to one or more moieties selected from groups as described above for the alkyl groups. Preferred cycloalkyl group is cycloheptyl.

The term "alkylene", as used herein, represents a divalent alkyl group, having straight or branched moieties, containing 1-12 carbon atoms, preferably 1-6 carbon atoms, and being optionally substituted with any suitable group, including but not limited to one or more moieties selected from groups as described above for the alkyl groups. Preferred alkylene groups are methylene, ethylene, hydroxyethylene, trimethylene or propylene.

The term "cycloalkenyl", as used herein, is defined as a cyclic unsaturated hydrocarbon radical having at least one double bond, containing 4-20 carbon atoms, preferably 5-8 carbon atoms, and being optionally substituted with any suitable group, including but not limited to one or more moieties selected from groups as described above for the alkyl groups. Preferred cycloalkenyl group is 6-(hydroxymethyl)cyclohex-3-en-1-yl.

The term "aryl", as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, nitro, C1-6-alkyl, C1-6-alkoxy, C1-6-alkylsulfonyl, trifluoromethylthio or pyridinylalkyl. Aryl radicals are preferably phenyl radicals. Preferred aryl groups are phenyl, 3-hydroxyphenyl, 3-fluorophenyl, 3-methylphenyl, 4-methylphenyl, 4-hydroxyphenyl, 4-hydroxy-3-methoxyphenyl, 3-(2-pyridin-2-ylethyl)phenyl, 3,4-dimethylphenyl, 4tert-butylphenyl, 4-methylsulfonylphenyl, 2-nitrophenyl, 2-chloro-6-fluorophenyl, 2-[(trifluoromethyl)thio]phenyl, 2-chlorophenyl or 4-bromophenyl.

The term "halogen", as used herein, includes an atom of Cl, Br, F, I.

The term "nitro", as used herein, represents a group of the formula —$NO_2$.

The term "hydroxy", as used herein, represents a group of the formula —OH.

The term "alkoxy", as used herein, represents a group of formula —$OR^b$ wherein $R^b$ is an alkyl group, as defined above.

The term "ester", as used herein, represents a group of formula —$COOR^c$ wherein $R^c$ is an alkyl group or an aryl group, as defined above.

The term "alkoxycarbonyl", as used herein, represents a group of formula —$COOR^d$ wherein $R^d$ is an alkyl group, as defined above.

The term "amino", as used herein, represents a group of the formula —$NH_2$.

The term "alkylamino", as used herein, represents a group of formula —$NHR^e$ or —$NR^eR^f$ wherein $R^e$ and $R^f$ are alkyl group as defined above.

The term alkylsulfonyl, as used herein is defined as representing a group of formula —$SO_2$—$R^g$, wherein $R^g$ is C1-4-alkyl.

The term "heterocycle", as used herein is defined as including an aromatic or non aromatic cycloalkyl or cycloalkenyl moiety as defined above, having at least one O, S and/or N atom interrupting the carbocyclic ring structure and optionally, one of the carbon of the carbocyclic ring structure may be replaced by a carbonyl.

Non-limiting examples of aromatic heterocycles are pyrazolyl, furyl, imidazolyl, triazolyl, oxazolyl, pyridinyl, pyrrolyl, thienyl, isothiazolyl, benzimidazolyl, tetrazolyl, isooxazolyl, oxazolyl, thiazolyl, 1,2,4-thiadiazolyl, oxadiazole, pyridazinyl, pyrimidinyl, pyrazinyl, isoindolyl, triazolopyridinyl, imidazolopyridinyl, pyrrolopyrimidinyl, pyrazolopyrimidinyl, quinazolinyl, quinolizinyl, naphthyridinyl, quinolyl, isoquinolyl, isobenzofuranyl, benzothienyl, indolyl, indolizinyl, purinyl, carbazolyl, thieno(2,3-b)furanyl, thianthrenyl, benzothiazolyl, benzoxazolyl, cinnolinyl, quinoxalinyl, phenothiazinyl, isochromanyl and xanthenyl, optionally substituted by 1 to 5 substituents independently selected from halogen, hydroxy, thiol, amino, nitro, cyano, azido, C1-6-alkoxy, C1-6-alkylthio, C1-6-alkyl, C1-6-haloalkyl, formyl or ester. More preferred aromatic heterocycles are pyrazolyl, furyl, imidazolyl, triazolyl, oxazolyl and pyridinyl.

Non-limiting examples of non aromatic heterocycles are tetrahydrofuranyl, piperidinyl, piperidyl, piperazinyl, imidazolidinyl, morpholinyl, thiomorpholinyl, pyrrolidinyl, thiazolidinyl, indolinyl, tetrahydrobenzazocinyl, dihydroisochromenyl, tetrahydropyranyl, oxooctahydroquinolinyl, dioxolanyl, 1-oxaspiro(4.5)dec-2-yl, pyrrolidinyl, 2-oxopyrrolidinyl, 8-thiabicyclo[3.2.1]cyclooctanyl, 1,4-dithiepanyl, tetrahydro-2H-thiopyranyl, azepanyl and azocanyl, optionally substituted by 1 to 5 substituents independently selected from halogen, hydroxy, thiol, amino, nitro, cyano, azido, C1-6-alkoxy, C1-6-alkylthio, C1-6-alkyl, C1-6-haloalkyl, formyl or ester. More preferred non aromatic heterocycles are tetrahydrofuranyl, piperidinyl, piperidyl, piperazinyl, imidazolidinyl, morpholinyl, thiomorpholinyl, pyrrolidinyl, thiazolidinyl, indolinyl, tetrahydro-1-benzazocin-1(2H)-yl, 3,4-dihydro-1H-isochromen-1-yl, tetrahydropyranyl, oxooctahydroquinolinyl and dioxolanyl. The term "heterocycle" also includes bicyclic, tricyclic and tetracyclic, spiro groups in which any of the above heterocyclic rings is fused to one or two rings independently selected from an aryl ring, a cycloalkyl ring, a cycloalkenyl ring or another monocyclic heterocyclic, ring or where a monocyclic heterocyclic group is bridged by an alkylene group, such as quinuclidinyl, 7-azabicyclo(2.2.1)heptanyl, 7-oxabicyclo(2.2.1)heptanyl and 8-azabicyclo(3.2.1)octanyl.

The term "pyridinylalkyl", as used herein, represents a group of formula —$R^h$— pyridinyl in which $R^h$ is C1-4-alkylene.

The term "azido" as used herein, represents a group of the formula —$N_3$.

The term "cyano" as used herein, represents a group of the formula —CN.

Generally, $R^2$ is hydrogen or C1-4-alkyl.

Preferably, $R^2$ is hydrogen, methyl or ethyl. More preferably, $R^2$ is hydrogen or methyl.

Generally, $R^3$ is hydrogen; C1-6-alkyl unsubstituted or substituted by 1 to 5 substituents selected from halogen, hydroxy, alkoxy, alkoxycarbonyl or alkylamino; C5-7-cycloalkyl; (hydroxymethyl)cyclohexenyl; phenyl unsubstituted or substituted by 1 to 5 substituents selected from halogen, C1-4-alkyl, hydroxy, methoxy, nitro, methylsulfonyl, trifluoromethylthio or pyridinylalkyl; pyridinyl unsubstituted or substituted by methoxy; triazolyl; C1-4-alkoxy; or a group of formula —W—$R^8$ wherein:

Generally, W is C1-4-alkylene unsubstituted or substituted by halogen, hydroxy, C1-4-alkyl or alkoxy; —NH—; or —NHC(=O)—; and $R^8$ is phenyl unsubstituted or substituted by 1 to 5 substituents selected from halogen, C1-4-alkyl, hydroxy, methoxy, nitro, methylsulfonyl or trifluoromethylthio; furyl unsubstituted or substituted by methyl; pyrazolyl; pyridinyl; morpholinyl; tetrahydrobenzazocinyl; piperidinyl unsubstituted or substituted by methyl; dihydroisochromenyl or dihydroimidazolyl.

Preferably, $R^3$ is hydrogen, n-butyl, cycloheptyl, 2-fluoroethyl, 3-hydroxypropyl, 3-hydroxy-2,2-dimethylpropyl, 1-(hydroxymethyl)propyl, 3,3,3-trifluoro-2-hydroxypropyl, 3-ethoxypropyl, 2-ethoxy-2-oxoethyl, 3-(dimethylamino)propyl, 6-(hydroxymethyl)cyclohex-3-en-1-yl, 3-hydroxyphenyl, 3-fluorophenyl, 3-(2-pyridin-2-ylethyl)phenyl, 3,4-dimethylphenyl, 4-tert-butylphenyl, benzyl, 4-hydroxy-3-methoxybenzyl, 4-methylsulfonylbenzyl, 2-nitrobenzyl, 2-chloro-6-fluorobenzyl, 2-[(trifluoromethyl)thio]benzyl, 2-hydroxy-2-phenylethyl, 2-(3,4-dimethoxyphenyl)ethyl, 2-(2-chlorophenyl)ethyl, 2-(4-methylphenyl)ethyl, (4-bromophenyl)amino, pyridin-3-yl, 6-methoxypyridin-3-yl, 4H-1,2,4-triazol-3-yl, pyridin-4-ylmethyl, (5-methyl-2-furyl)methyl, 3-(1H-pyrazol-1-yl)propyl, 2-morpholin-4-ylethyl, 2-((3,4,5,6-tetrahydro-1-benzazocin-1(2H)-yl)propyl, 2-(2-methylpiperidin-1-yl)ethyl, 3,4-dihydro-1H-isochromen-1-ylmethyl, methoxy, (4-pyridinylcarbonyl)amino or 4,5-dihydro-1H-imidazol-2-ylamino. More preferably, $R^3$ is hydrogen.

Generally, $R^{3a}$ is hydrogen, C1-4-alkyl or a group of formula

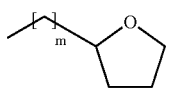

wherein m is 1 to 4.

Preferably, $R^{3a}$ is hydrogen, methyl or tetrahydrofuran-2-ylmethyl. More preferably, $R^{3a}$ is hydrogen.

In another embodiment, $NR^3R^{3a}$ is piperidinyl unsubstituted or substituted by hydroxy; thiomorpholinyl; thiazolidinyl unsubstituted or substituted by C1-4-alkoxycarbonyl; 2,5-dihydro-1H-pyrrol-1-yl; 1,4-dioxa-8-azaspiro[4.5]dec-8-yl; 4-oxooctahydro-1(2H)-quinolinyl; or a group of formula

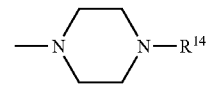

wherein $R^{14}$ is pyridinyl; phenyl unsubstituted or substituted by halogen, hydroxy, C1-4-alkyl; or a group of formula —V—$R^{15}$ wherein V is unsubstituted C1-4-alkylene and $R^{15}$ is phenyl or morpholinyl.

In a preferred embodiment, $NR^3R^{3a}$ is 4-pyridin-2-ylpiperazin-1-yl, 4-(3-methylphenyl)piperazin-1-yl, 4-(4-hydroxyphenyl)piperazin-1-yl, 4-(2-phenylethyl)piperazin-1-yl, 4-(2-morpholin-4-ylethyl)piperazin-1-yl, 3-hydroxypiperidin-1-yl, thiomorpholin-4-yl, 4-methoxycarbonyl-1,3-thiazolidin-3-yl, 2,5-dihydro-1H-pyrrol-1-yl, 1,4-dioxa-8-azaspiro[4.5]dec-8-yl or 4-oxooctahydro-1(2H)-quinolinyl.

Generally, $R^5$ is hydrogen, nitro, halogen, C1-4-alkyl, unsubstituted or substituted by halogen, or C1-4-alkoxy unsubstituted or substituted by halogen.

Preferably, $R^5$ is hydrogen, methyl, ethyl, trifluoromethyl, trifluoromethoxy, n-propyl, isopropyl, nitro, or halogen. More preferably, $R^5$ is halogen or trifluoromethyl.

Generally, $R^6$ is hydrogen, C1-6-alkyl or halogen.

Preferably, $R^6$ is hydrogen, methyl or Cl. More preferably, $R^6$ is hydrogen.

Generally, $R^7$ is hydrogen, methyl or halogen.

Preferably, $R^7$ is hydrogen, methyl, Br, F or Cl. More preferably, $R^7$ is hydrogen, Br or F.

Combinations of one or more of these preferred compound groups are especially preferred.

In a preferred embodiment, the invention provides a compound having the formula I or a pharmaceutically acceptable salt thereof or stereoisomeric forms thereof,

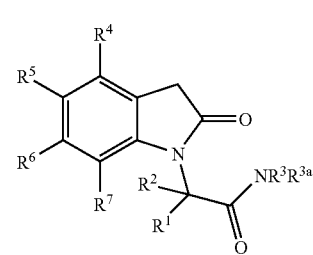

(I)

wherein
$R^1$ is hydrogen,
$R^2$ is hydrogen or C1-4-alkyl,
$R^3$ is hydrogen; C1-6-alkyl unsubstituted or substituted by 1 to 5 substituents selected from halogen, hydroxy, alkoxy, alkoxycarbonyl or alkylamino; C5-7-cycloalkyl; (hydroxymethyl)cyclohexenyl; phenyl unsubstituted or substituted by 1 to 5 substituents selected from halogen, C1-4-alkyl, hydroxy, methoxy, nitro, methylsulfonyl, trifluoromethylthio or pyridinylalkyl; pyridinyl unsubstituted or substituted by methoxy; triazolyl; C1-4-alkoxy; or a group of formula —W—$R^8$, $R^{3a}$ is hydrogen, C1-4-alkyl or a group of formula

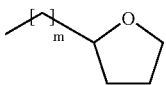

or $NR^3R^{3a}$ is piperidinyl unsubstituted or substituted by hydroxy; thiomorpholinyl; thiazolidinyl unsubstituted or substituted by C1-4-alkoxycarbonyl; 2,5-dihydro-1H-pyrrol-1-yl; 1,4-dioxa-8-azaspiro[4.5]dec-8-yl; 4-oxooctahydro-1(2H)-quinolinyl; or a group of formula

$R^4$ is hydrogen,
$R^5$ is hydrogen; nitro; halogen; C1-4-alkyl, unsubstituted or substituted by halogen; or C1-4-alkoxy unsubstituted or substituted by halogen,
$R^6$ is hydrogen, C1-6-alkyl or halogen,
$R^7$ is hydrogen, methyl or halogen,
W is C1-4-alkylene unsubstituted or substituted by halogen, hydroxy, C1-4-alkyl or alkoxy; —NH—; or —NHC(=O)—,
$R^8$ is phenyl unsubstituted or substituted by 1 to 5 substituents selected from halogen, C1-4-alkyl, hydroxy, methoxy, nitro, methylsulfonyl or trifluoromethylthio; furyl unsubstituted or substituted by methyl; pyrazolyl; pyridinyl; morpholinyl; tetrahydrobenzazocinyl; piperidinyl unsubstituted or substituted by methyl; dihydroisochromenyl or dihydroimidazolyl,
$R^{14}$ is pyridinyl; phenyl unsubstituted or substituted by halogen, hydroxy, C1-4-alkyl;

or a group of formula —V—$R^{15}$,
V is unsubstituted C1-4-alkylene,
$R^{15}$ is phenyl or morpholinyl,
m is 1 to 4, and at least one of $R^5$, $R^6$ or $R^7$ is different from hydrogen when $R^2$ is hydrogen, $R^3$ is H or 2,6-diisopropylphenyl, and $R^{3a}$ is H.

In a more preferred embodiment, the invention provides a compound having the formula I or a pharmaceutically acceptable salt thereof or stereoisomeric forms thereof,

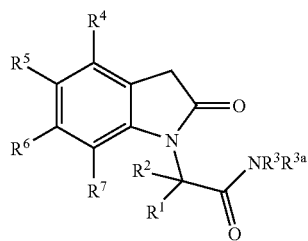

(I)

wherein
$R^1$ is hydrogen,
$R^2$ is hydrogen, methyl or ethyl, $R^3$ is hydrogen, n-butyl, cycloheptyl, 2-fluoroethyl, 3-hydroxypropyl, 3-hydroxy-2,2-dimethylpropyl, 1-(hydroxymethyl)propyl, 3,3,3-trifluoro-2-hydroxypropyl, 3-ethoxypropyl, 2-ethoxy-2-oxoethyl, 3-(dimethylamino)propyl, 6-(hydroxymethyl)cyclohex-3-en-1-yl, 3-hydroxyphenyl, 3-fluorophenyl, 3-(2-pyridin-2-ylethyl)phenyl, 3,4-dimethylphenyl, 4-tert-butylphenyl, benzyl, 4-hydroxy-3-methoxybenzyl, 4-methylsulfonylbenzyl, 2-nitrobenzyl, 2-chloro-6-fluorobenzyl, 2-[(trifluoromethyl)thio]benzyl, 2-hydroxy-2-phenylethyl, 2-(3,4-dimethoxyphenyl)ethyl, 2-(2-chlorophenyl)ethyl, 2-(4-methylphenyl)ethyl, (4-bromophenyl)amino, pyridin-3-yl, 6-methoxypyridin-3-yl, 4H-1,2,4-triazol-3-yl, pyridin-4-ylmethyl, (5-methyl-2-furyl)methyl, 3-(1H-pyrazol-1-yl)propyl, 2-morpholin-4-ylethyl, 2-((3,4,5,6-tetrahydro-1-benzazocin-1(2H)-yl)propyl, 2-(2-methylpiperidin-1-yl)ethyl, 3,4-dihydro-1H-isochromen-1-ylmethyl, methoxy, (4-pyridinylcarbonyl)amino or 4,5-dihydro-1H-imidazol-2-ylamino,
$R^{3a}$ is hydrogen, methyl or tetrahydrofuran-2-ylmethyl,
or $NR^3R^{3a}$ 4-pyridin-2-ylpiperazin-1-yl, 4-(3-methylphenyl)piperazin-1-yl, 4-(4-hydroxyphenyl)piperazin-1-yl, 4-(2-phenylethyl)piperazin-1-yl, 4-(2-morpholin-4-ylethyl)piperazin-1-yl, 3-hydroxypiperidin-1-yl, thiomorpholin-4-yl, 4-methoxycarbonyl-1,3-thiazolidin-3-yl, 2,5-dihydro-1H-pyrrol-1-yl, 1,4-dioxa-8-azaspiro[4.5]dec-8-yl or 4-oxooctahydro-1(2H)-quinolinyl,
$R^4$ is hydrogen,
$R^5$ is hydrogen, methyl, ethyl, trifluoromethyl, trifluoromethoxy, n-propyl, isopropyl, nitro or halogen,
$R^6$ is hydrogen, methyl or Cl,
$R^7$ is hydrogen, methyl, Br, F or Cl,
and at least one of $R^5$, $R^6$ or $R^7$ is different from hydrogen when $R^2$ is hydrogen, $R^3$ is H or 2,6-diisopropylphenyl, and $R^{3a}$ is H.

More preferably, $R^2$ is hydrogen or methyl, $R^3$ is hydrogen, $R^{3a}$ is hydrogen, $R^5$ is halogen or trifluoromethyl, $R^6$ is hydrogen and $R^7$ is hydrogen, Br or F.

In all the above-mentioned scopes, when $R^2$ is C1-20-alkyl, the carbon atom to which $R^2$ is attached is preferably in the "S"-configuration.

Preferred compounds are: 2-(5-iodo-2-oxo-2,3-dihydro-1H-indol-1-yl)acetamide; 2-(5-chloro-2-oxo-2,3-dihydro-1H-indol-1-yl)acetamide; 2-(5,7-dibromo-2-oxo-2,3-dihydro-1H-indol-1-yl)acetamide; 2-(5-nitro-2-oxo-2,3-dihydro-1H-indol-1-yl)acetamide; 2-(5-methyl-2-oxo-2,3-dihydro-1H-indol-1-yl)acetamide; 2-(5-chloro-2-oxo-2,3-dihydro-1H-indol-1-yl)propanamide; (2R)-2-(5-chloro-2-oxo-2,3-dihydro-1H-indol-1-yl)propanamide; (2S)-2-(5-chloro-2-oxo-2,3-dihydro-1H-indol-1-yl)propanamide; 2-[2-oxo-5-(trifluoromethoxy)-2,3-dihydro-1H-indol-1-yl]acetamide; 2-(5-isopropyl-2-oxo-2,3-dihydro-H-indol-1-yl)acetamide; 2-(5-ethyl-2-oxo-2,3-dihydro-1H-indol-1-yl)acetamide; 2-(5-fluoro-2-oxo-2,3-dihydro-1H-indol-1-yl)acetamide; 2-(5,7-dimethyl-2-oxo-2,3-dihydro-1H-indol-1-yl)acetamide; 2-(5-bromo-2-oxo-2,3-dihydro-1H-indol-1-yl)acetamide; 2-(2-oxo-5-propyl-2,3-dihydro-1H-indol-1-yl)acetamide; 2-[2-oxo-5-(trifluoromethyl)-2,3-dihydro-1H-indol-1-yl]acetamide; 2-(5,6-dimethyl-2-oxo-2,3-dihydro-1H-indol-1-yl)acetamide; 2-(7-chloro-2-oxo-2,3-dihydro-1H-indol-1-yl)acetamide; 2-(6-chloro-2-oxo-2,3-dihydro-1H-indol-1-yl)acetamide; 2-(5-chloro-2-oxo-2,3-dihydro-1H-indol-1-yl)butanamide; (+)-2-(5-chloro-2-oxo-2,3-dihydro-1H-indol-1-yl)butanamide; (−)-2-(5-chloro-2-oxo-2,3-dihydro-1H-indol-1-yl)butanamide; 2-(5-methyl-2-oxo-2,3-dihydro-1H-indol-1-yl)propanamide; (+)-2-(5-methyl-2-oxo-2,3-dihydro-1H-indol-1-yl)propanamide; (−)-2-(5-methyl-2- oxo-2,3-dihydro-1H-indol-1-yl)propanamide; 2-(5-bromo-2-oxo-2,3-dihydro-1H-indol-1-yl)propanamide; (−)-2-(5-bromo-2-oxo-2,3-dihydro-1H-indol-1-yl)propanamide; (+)-2-(5-bromo-2-oxo-2,3-dihydro-1H-indol-1-yl)propanamide; 2-(5-chloro-7-fluoro-2-oxo-2,3-dihydro-1H-indol-1-yl)acetamide; 2-(5-chloro-2-oxo-2,3-dihydro-1H-indol-1-yl)-N-(3-hydroxyphenyl)acetamide; 2-(5-chloro-2-oxo-2,3-dihydro-1H-indol-1-yl)-N-(3-fluorophenyl)acetamide; 2-(5-chloro-2-oxo-2,3-dihydro-1H-indol-1-yl)-N-[3-(2-pyridin-2-ylethyl)phenyl]acetamide; 2-(5-chloro-2-oxo-2,3-dihydro-1H-indol-1-yl)-N-[6-(hydroxymethyl)cyclohex-3-en-1-yl]acetamide; 5-chloro-1-[2-oxo-2-(4-pyridin-2-ylpiperazin-1-yl)ethyl]-1,3-dihydro-2H-indol-2-one; 5-chloro-1-{2-[4-(3-methylphenyl)piperazin-1-yl]-2-oxoethyl}-1,3-dihydro-2H-indol-2-one; 2-(5-chloro-2-oxo-2,3-dihydro-1H-indol-1-yl)-N-(4-hydroxy-3-methoxybenzyl)acetamide; 2-(5-chloro-2-oxo-2,3-dihydro-1H-indol-1-yl)-N-(pyridin-4-ylmethyl)-N-(tetrahydrofuran-2-ylmethyl)acetamide; 5-chloro-1-[2-(3-hydroxypiperidin-1-yl)-2-oxoethyl]-1,3-dihydro-2H-indol-2-one; 2-(5-chloro-2-oxo-2,3-dihydro-1H-indol-1-yl)-N'-isonicotinoylacetohydrazide; 5-chloro-1-(2-oxo-2-thiomorpholin-4-ylethyl)-1,3-dihydro-2H-indol-2-one; 2-(5-chloro-2-oxo-2,3-dihydro-1H-indol-1-yl)-N-(4H-1,2,4-triazol-3-yl)acetamide; 2-(5-chloro-2-oxo-2,3-dihydro-1H-indol-1-yl)-N-[4-(methylsulfonyl)benzyl]acetamide; 1-[(5-chloro-2-oxo-2,3-dihydro-1H-indol-1-yl)acetyl]octahydroquinolin-4(1H)-one; N'-(4-bromophenyl)-2-(5-chloro-2-oxo-2,3-dihydro-1H-indol-1-yl)acetohydrazide; 2-(5-chloro-2-oxo-2,3-dihydro-1H-indol-1-yl)-N-(6-methoxypyridin-3-yl)acetamide; N-butyl-2-(5-chloro-2-oxo-2,3-dihydro-1H-indol-1-yl)acetamide; 2-(5-chloro-2-oxo-2,3-dihydro-1H-indol-1-yl)-N-(3-hydroxypropyl)acetamide; 2-(5-chloro-2-oxo-2,3-dihydro-1H-indol-1-yl)-N-[3-(dimethylamino)propyl]acetamide; 5-chloro-1-{2-oxo-2-[4-(2-phenylethyl)piperazin-1-yl]ethyl}-1,3-dihydro-2H-indol-2-one; ethyl{[(5-chloro-2-oxo-2,3-dihydro-1H-indol-1-yl)acetyl]amino}acetate; 2-(5-chloro-2-oxo-2,3-dihydro-1H-indol-1-yl)-N-(3-ethoxypropyl)acetamide; 2-(5-chloro-2-oxo-2,3-dihydro-1H-indol-1-yl)-N-(2-fluoroethyl)acetamide; 2-(5-chloro-2-oxo-2,3-dihydro-1H-indol-1-yl)-N-methoxy-N-methylacetamide; 2-(5-chloro-2-oxo-2,3-dihydro-1H-indol-1-yl)-N-(3,4-dimethylphenyl)acetamide; N-(4-tert-butylphenyl)-2-(5-chloro-2-oxo-2,3-dihydro-1H-indol-1-yl)acetamide; 2-(5-chloro-2-oxo-2,3-dihydro-1H-indol-1-yl)-N-(3-hydroxy-2,2-dimethylpropyl)acetamide; 2-(5-chloro-2-oxo-2,3-dihydro-1H-indol-1-yl)-N-[1-(hydroxymethyl)propyl]acetamide; 2-(5-chloro-2-oxo-2,3-dihydro-1H-indol-1-yl)-N-(3,3,3-trifluoro-2-hydroxypropyl)acetamide; 2-(5-chloro-2-oxo-2,3-dihydro-1H-indol-1-yl)-N-(2-hydroxy-2-phenylethyl)acetamide; 5-chloro-1-{2-[4-(4-hydroxyphenyl)piperazin-1-yl]-2-oxoethyl}-1,3-dihydro-2H-indol-2-one; 2-(5-chloro-2-oxo-2,3-dihydro-1H-indol-1-yl)-N-(pyridin-4-ylmethyl)acetamide; 2-(5-chloro-2-oxo-2,3-dihydro-1H-indol-1-yl)-N-[(5-methyl-2-furyl)methyl]acetamide; 2-(5-chloro-2-oxo-2,3-dihydro-1H-indol-1-yl)-N-[3-(1H-pyrazol-1-yl)propyl]acetamide; methyl 3-[(5-chloro-2-oxo-2,3-dihydro-1H-indol-1-yl)acetyl]-1,3-thiazolidine-4-carboxylate; 5-chloro-1-[2-(2,5-dihydro-1H-pyrrol-1-yl)-2-oxoethyl]-1,3-dihydro-2H-indol-2-one; 2-(5-chloro-2-oxo-2,3-dihydro-1H-indol-1-yl)-N'-(4,5-dihydro-1H-imidazol-2-yl)acetohydrazide; 2-(5-chloro-2-oxo-2,3-dihydro-1H-indol-1-yl)-N-[2-(3,4-dimethoxyphenyl)ethyl]acetamide; 2-(5-chloro-2-oxo-2,3-dihydro-1H-indol-1-yl)-N-[2-(2-chlorophenyl)ethyl]acetamide; 2-(5-chloro-2-oxo-2,3-dihydro-1H-indol-1-yl)-N-[2-(4-methylphenyl)ethyl]acetamide; 2-(5-chloro-2-oxo-2,3-dihydro-1H-indol-1-yl)-N-(2-morpholin-4-ylethyl)acetamide; 2-(5-chloro-2-oxo-2,3-dihydro-1H-indol-1-yl)-N-[2-(3,4,5,6-tetrahydro-1-benzazocin-1(2H)-yl)propyl]acetamide; 2-(5-chloro-2-oxo-2,3-dihydro-1H-indol-1-yl)-N-[2-(2-methylpiperidin-1-yl)ethyl]acetamide; 2-(5-chloro-2-oxo-2,3-dihydro-1H-indol-1-yl)-N-(2-nitrobenzyl)acetamide; 2-(5-chloro-2-oxo-2,3-dihydro-1H-indol-1-yl)-N-(3,4-dihydro-1H-isochromen-1-ylmethyl)acetamide; N-(2-chloro-6-fluorobenzyl)-2-(5-chloro-2-oxo-2,3-dihydro-1H-indol-1-yl)acetamide; N-benzyl-2-(5-chloro-2-oxo-2,3-dihydro-1H-indol-1-yl)-N-methylacetamide; 2-(5-chloro-2-oxo-2,3-dihydro-1H-indol-1-yl)-N-{2-[(trifluoromethyl)thio]benzyl}acetamide; 5-chloro-1-[2-(1,4-dioxa-8-azaspiro[4.5]dec-8-yl)-2-oxoethyl]-1,3-dihydro-2H-indol-2-one; 2-(5-chloro-2-oxo-2,3-dihydro-1H-indol-1-yl)-N-cycloheptylacetamide; 5-chloro-1-{2-[4-(2-morpholin-4-ylethyl)piperazin-1-yl]-2-oxoethyl}-1,3-dihydro-2H-indol-2-one; and 2-(5-chloro-2-oxo-2,3-dihydro-1H-indol-1-yl)-N-pyridin-3-ylacetamide.

More preferred compounds are: 2-(5-iodo-2-oxo-2,3-dihydro-1H-indol-1-yl)acetamide; 2-(5-chloro-2-oxo-2,3-dihydro-1H-indol-1-yl)acetamide; 2-(5,7-dibromo-2-oxo-2,3-dihydro-1H-indol-1-yl)acetamide; (2S)-2-(5-chloro-2-oxo-2,3-dihydro-1H-indol-1-yl)propanamide; 2-[2-oxo-5-(trifluoromethyl)-2,3-dihydro-1H-indol-1-yl]acetamide and 2-(5-chloro-7-fluoro-2-oxo-2,3-dihydro-1H-indol-1-yl)acetamide.

In a most preferred embodiment the invention relates to a compound selected from 2-(5-chloro-2-oxo-2,3-dihydro-1H-indol-1-yl)acetamide and (2S)-2-(5-chloro-2-oxo-2,3-dihydro-1H-indol-1-yl)propanamide.

The "pharmaceutically acceptable salts" according to the invention include therapeutically active, non-toxic base salt forms which the compounds of formula I are able to form.

The compounds of formula I containing acidic protons may be converted into their therapeutically active, non-toxic base addition salt forms, e.g. metal or amine salts, by treatment with appropriate organic and inorganic bases. Appropriate base salt forms include, for example but not limited to, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

Some of the compounds of formula I may also exist in tautomeric forms. Such forms although not explicity indicated in the above formula are intended to be included within the scope of the present invention.

With respect to the present invention reference to a compound or compounds is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of formula I according to the invention can be prepared analogously to conventional methods as understood by the person skilled in the art of synthetic organic chemistry.

A. According to one embodiment, some compounds having the general formula I may be prepared by desulfurization of a compound of formula II according to the equation:

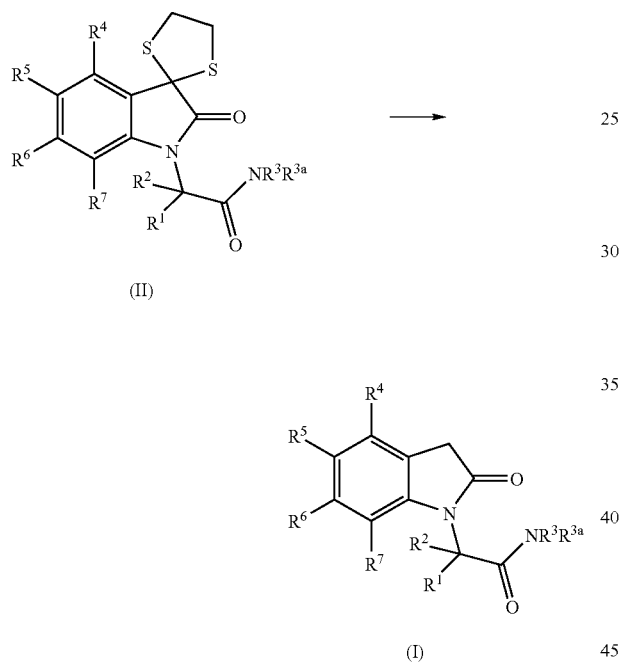

This reaction may be carried out using Raney nickel in an inert solvent, preferably THF, at a temperature comprised between 0° C. and 40° C., or as described in: Mehta L., Parrick J., Payne F., J. Chem. Research (S) (1998), 190-191.

Compounds of formula II may be prepared by alkylation of a compound of formula III with a compound of formula IV according to the equation:

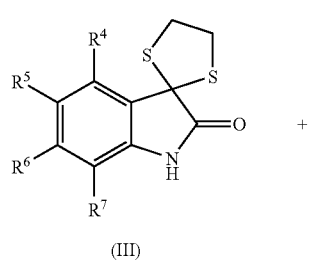

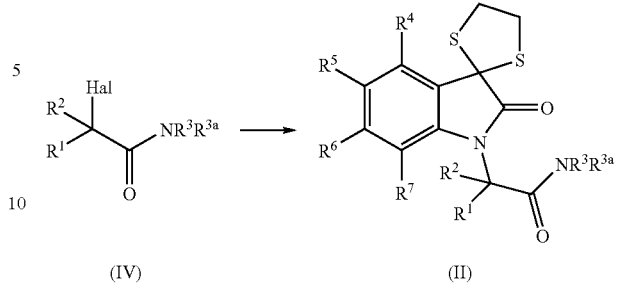

wherein Hal is a halogen atom, preferably Br or Cl, and $R^1$, $R^2$, $R^3$, $R^{3a}$, $R^4$, $R^5$ and $R^7$ have the same definitions as described above.

This reaction may be carried out with a strong base, for example sodium hydride, at a temperature comprised between 0 and 40° C. and in an inert solvent, for example DMF under an inert atmosphere, or as described in patent GB 1,309,692 (UCB).

Compounds of formula III may be prepared by reaction of a compound of formula V with 1,2-ethanedithiol according to the equation:

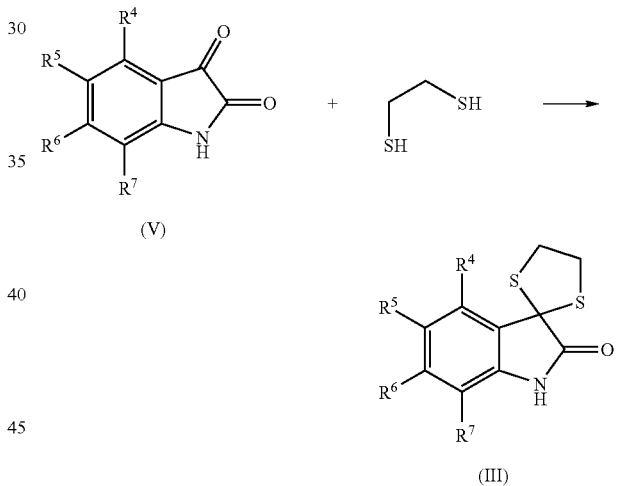

wherein $R^4$, $R^5$ and $R^7$ have the same definitions as described above.

This reaction may be carried out at a temperature comprised between 25 and 100° C. in an inert solvent or in acetic acid, in the presence of a Lewis acid, preferably $BF_3.Et_2O$ under an inert atmosphere.

Compounds of formula V are commercially available or may be prepared according to methods described in: Smith K, El-Hiti G. A., Hawes A. C., Synlett (1999), 945-947; Lackey K, Sternbach D. D., Synthesis (1993), 10, 993; or Organic Synthesis, Collective Volume I, Second Edition, Gilman H. & Blatt A. H., J. Wiley & Sons Inc., 327-330.

B. According to another embodiment, some compounds having the general formula I may be prepared by oxidative bromination of the corresponding indole of formula (VI) followed by the reduction of compound (VII) according to the equation:

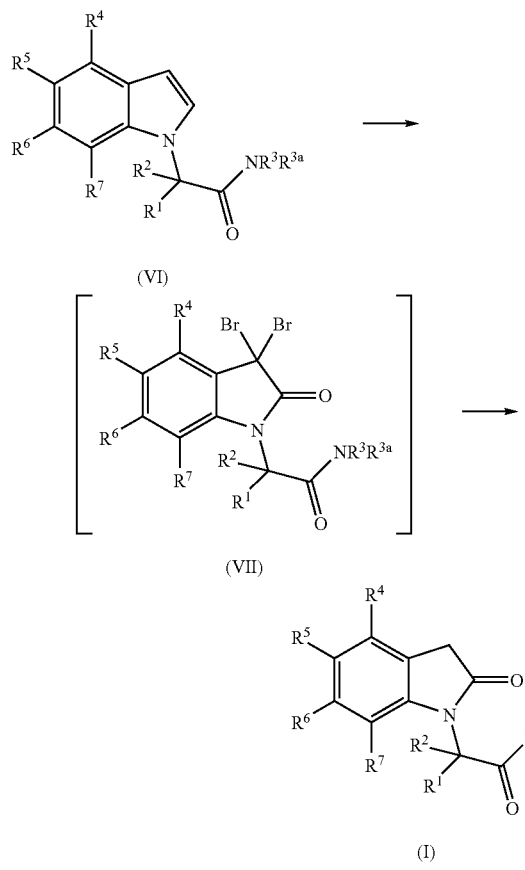

This reaction may be carried out as described in: Marfat A., Carta M. P., Tetrahedron Lett. (1987), 28, 4027-4031.

Compounds of formula VI may be prepared by alkylation of a compound of formula VIII with a compound of formula IV according to the equation:

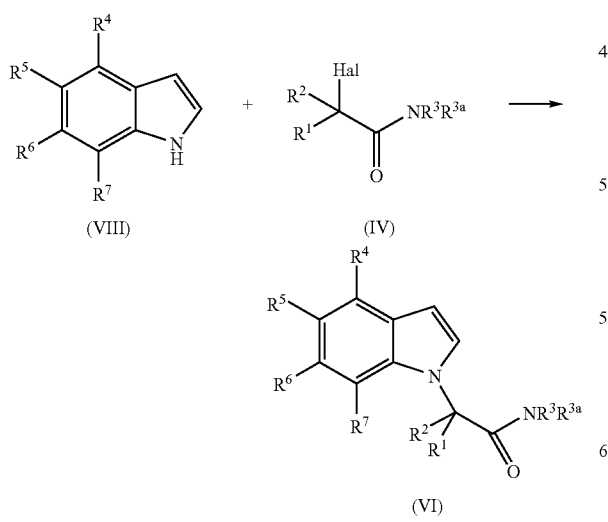

wherein Hal is an halogen atom, preferably Br or Cl.

This reaction may be carried out in the presence of a strong base, preferably sodium hydride, at a temperature comprised between 0 and 40° C., in an inert solvent, for example DMF, under an inert atmosphere, or as described in patent GB 1,309,692 (UCB).

C. According to another embodiment, some compounds having the general formula I may be prepared by halogenation of the corresponding compound of formula I wherein $R^5$ is a hydrogen with a N-halosuccinimide according to the procedure described in: Castanet A.-S., Colobert F., Broutin P.-E., Tetrahedron Lett. (2002), 43, 5047-5048.

According to another embodiment, some compounds having the general formula I may be prepared analogously from the corresponding compound of formula I wherein $R^5=R^7=H$ by using two equivalents of N-halosuccinimide.

D. According to another embodiment, some compounds having the general formula I may be prepared by nitration of the corresponding compound of formula I wherein $R^5$ is a hydrogen according to procedure described in: Sun L., Rubin J. R., Kraker A. J., Showalter H. D., J. Heterocyclic Chem. (1997), 34, 1399-1405.

E. According to another embodiment, some compounds having the general formula I may be prepared by coupling of an amine of formula $NHR^3R^{3a}$ with a carboxylic acid derivative of formula IX in the presence of a coupling agent such as dicyclohexylcarbodiimide in dichloromethane or THF.

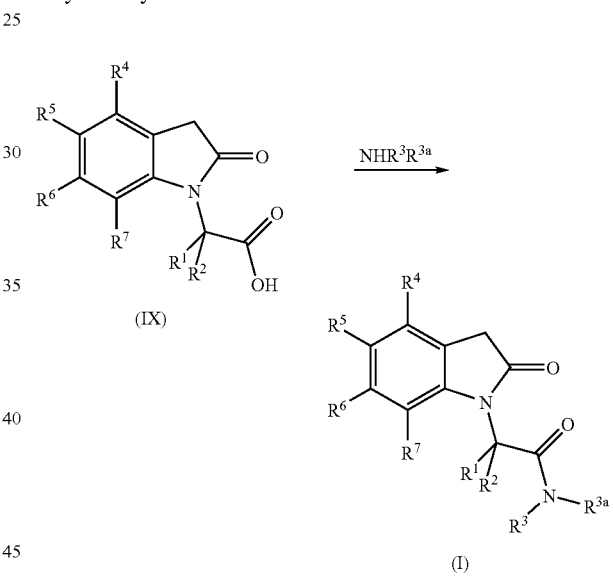

In one embodiment, the present invention concerns also the synthesis intermediates of formula II or stereoisomeric forms thereof,

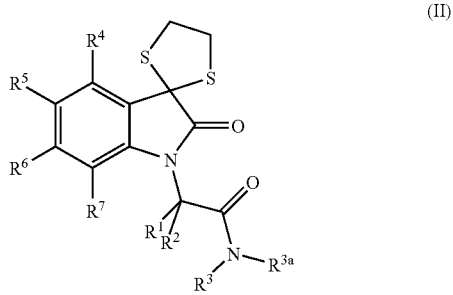

wherein
$R^1$ is hydrogen, $R^2$ is hydrogen or C1-20-alkyl,
$R^3$ is hydrogen, C1-20-alkyl, C4-8-cycloalkyl, C5-8-cycloalkenyl, aryl, aromatic or non aromatic heterocycle, C1-20-alkoxy, or a group of formula —W—$R^8$,
$R^{3a}$ is hydrogen, C1-20-alkyl or a group of formula:

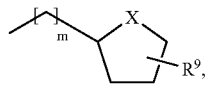

or $NR^3R^{3a}$ is a group of formula

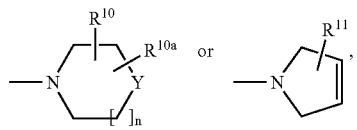

$R^4$ is hydrogen,
$R^5$ is hydrogen; nitro; halogen; azido; cyano; —S—C1-4-alkyl; —SO—C1-4-alkyl; —$SO_2$—C1-4-alkyl; —$SONH_2$; C1-20-alkyl unsubstituted or substituted by halogen; or C1-20-alkoxy unsubstituted or substituted by halogen,
$R^6$ is hydrogen, C1-20-alkyl or halogen,
$R^7$ is hydrogen, C1-20-alkyl or halogen,
W is C1-12-alkylene, —NH— or —NHC(=O)—,
X is O, S or NH,
Y is O, S, —$CR^{12}R^{13}$—, —$NR^{14}$— or —C(=O)—,
$R^8$ is aryl or heterocycle,
$R^9$, $R^{10}$, $R^{10a}$ and $R^{11}$ are independently selected from hydrogen, C1-4-alkyl, halogen, hydroxy or methoxycarbonyl,
or $R^{10}$ and $R^{10a}$ together form a C3-6-alkylene,
$R^{12}$ is hydrogen, C1-4-alkyl, halogen or hydroxy,
$R^{13}$ is hydrogen,
or $CR^{12}R^{13}$ is dioxolanyl,
$R^{14}$ is aryl, heterocycle or a group of formula —V—$R^{15}$,
V is C1-12-alkylene,
$R^{15}$ is aryl or heterocycle,
m is 1 to 4,
n is 0 or 1,
and at least one of $R^5$, $R^6$ or $R^7$ is different from hydrogen when $R^2$ is hydrogen, $R^3$ is H or 2,6-diisopropylphenyl, and $R^{3a}$ is H.

In another embodiment, the present invention concerns also the synthesis intermediates of formula II or stereoisomeric forms thereof,

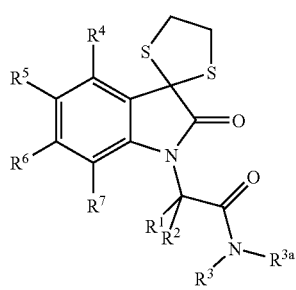
(II)

wherein
$R^1$ is hydrogen,
$R^2$ is hydrogen or C1-20-alkyl,
$R^3$ is hydrogen, C1-20-alkyl, C4-8-cycloalkyl, C5-8-cycloalkenyl, aryl, aromatic or non aromatic heterocycle, C1-20-alkoxy, or a group of formula —W—$R^8$,
$R^{3a}$ is hydrogen, C1-20-alkyl or a group of formula:

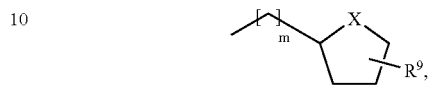

or $NR^3R^{3a}$ is a group of formula

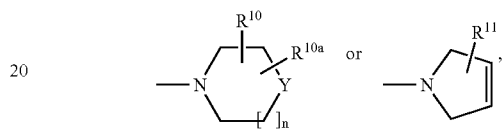

$R^4$ is hydrogen,
$R^5$ is hydrogen; nitro; halogen; C1-20-alkyl unsubstituted or substituted by halogen; or C1-20-alkoxy unsubstituted or substituted by halogen,
$R^6$ is hydrogen, C1-20-alkyl or halogen,
$R^7$ is hydrogen, C1-20-alkyl or halogen,
W is C1-12-alkylene, —NH— or —NHC(=O)—,
X is O, S or NH,
Y is O, S, —$CR^{12}R^{13}$—, —$NR^{14}$— or —C(=O)—,
$R^8$ is aryl or heterocycle,
$R^9$, $R^{10}$, $R^{10a}$ and $R^{11}$ are independently selected from hydrogen, C1-4-alkyl, halogen, hydroxy or methoxycarbonyl,
or $R^{10}$ and $R^{10a}$ together form a C3-6-alkylene,
$R^{12}$ is hydrogen, C1-4-alkyl, halogen or hydroxy,
$R^{13}$ is hydrogen,
or $CR^{12}R^{13}$ is dioxolanyl,
$R^{14}$ is aryl, heterocycle or a group of formula —V—$R^{15}$,
V is C1-12-alkylene,
$R^{15}$ is aryl or heterocycle,
m is 1 to 4,
n is 0 or 1,
and at least one of $R^5$, $R^6$ or $R^7$ is different from hydrogen when $R^2$ is hydrogen, $R^3$ is H or 2,6-diisopropylphenyl, and $R^{3a}$ is H.

Preferably, the synthesis intermediates of formula II are selected from the group consisting of: 2-(5'-methyl-2'-oxospiro[1,3-dithiolane-2,3'-indol]-1'(2'H)-yl)acetamide; 2-[2'-oxo-5'-[(trifluoromethyl)oxy]spiro[1,3-dithiolane-2,3'-indol]-1'(2'H)-yl]acetamide; 2-[5'-(1-methylethyl)-2'-oxospiro[1,3-dithiolane-2,3'-indol]-1'(2'H)-yl]acetamide; 2-(5'-ethyl-2'-oxospiro[1,3-dithiolane-2,3'-indol]-1'(2'H)-yl)acetamide; 2-(5'-fluoro-2'-oxospiro[1,3-dithiolane-2,3'-indol]-1'(2'H)-yl)acetamide; 2-(5',7'-dimethyl-2'-oxospiro[1,3-dithiolane-2,3'-indol]-1'(2'H)-yl)acetamide; 2-(2'-oxo-5'-propylspiro[1,3-dithiolane-2,3'-indol]-1'(2'H)-yl)acetamide; 2-[2'-oxo-5'-(trifluoromethyl)spiro[1,3-dithiolane-2,3'-indol]-1'(2'H)-yl]acetamide; and 2-(5',6'-dimethyl-2'-oxospiro[1,3-dithiolane-2,3'-indol]-1'(2'H)-yl)acetamide.

In one embodiment, the invention concerns also the synthesis intermediates of formula III or stereoisomeric forms thereof,

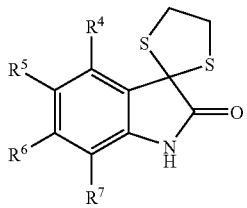

(III)

wherein

R⁴ is hydrogen,

R⁵ is hydrogen; nitro; azido; cyano, —S—C1-4-alkyl; —SO—C1-4-alkyl; —SO₂-C1-4-alkyl; —SONH₂; C1-20-alkyl unsubstituted or substituted by halogen; or C1-20-alkoxy unsubstituted or substituted by halogen, R⁶ is hydrogen, C1-20-alkyl or halogen, R⁷ is hydrogen, C1-20-alkyl or halogen, and at least one of R⁵, R⁶ or R⁷ is different from hydrogen.

In another embodiment, the invention concerns also the synthesis intermediates of formula III or stereoisomeric forms thereof,

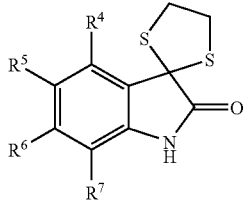

(III)

wherein

R⁴ is hydrogen,

R⁵ is hydrogen; nitro; C1-20-alkyl unsubstituted or substituted by halogen; or C1-20-alkoxy unsubstituted or substituted by halogen, R⁶ is hydrogen, C1-20-alkyl or halogen, R⁷ is hydrogen, C1-20-alkyl or halogen, and at least one of R⁵, R⁶ or R⁷ is different from hydrogen.

Preferably, the synthesis intermediates of formula III are selected from the group consisting of: 5'-methylspiro[1,3-dithiolane-2,3'-indol]-2'(1'H)-one; 5'-[(trifluoromethyl)oxy]spiro[1,3-dithiolane-2,3'-indol]-2'(1'H)-one; 5'-(1-methylethyl)spiro[1,3-dithiolane-2,3'-indol]-2'(1'H)-one; 5'-ethylspiro[1,3-dithiolane-2,3'-indol]-2'(1'H)-one; 5'-fluorospiro[1,3-dithiolane-2,3'-indol]-2'(1'H)-one; 5',7'-dimethylspiro[1,3-dithiolane-2,3'-indol]-2'(1'H)-one; 5'-propylspiro[1,3-dithiolane-2,3'-indol]-2'(1'H)-one; 5'-(trifluoromethyl)spiro[1,3-dithiolane-2,3'-indol]-2'(1'H)-one; and 5',6'-dimethylspiro[1,3-dithiolane-2,3'-indol]-2'(1'H)-one.

In one embodiment, the present invention concerns also the synthesis intermediates of formula VI or stereoisomeric forms thereof,

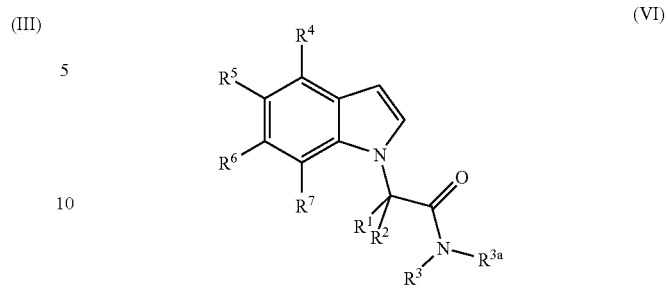

(VI)

wherein

R¹ is hydrogen,

R² is hydrogen or C1-20-alkyl,

R³ is hydrogen, C1-20-alkyl, C4-8-cycloalkyl, C5-8-cycloalkenyl, aryl, aromatic or non aromatic heterocycle, C1-20-alkoxy, or a group of formula —W—R⁸, R³ᵃ is hydrogen, C1-20-alkyl or a group of formula:

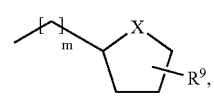

or NR³R³ᵃ is a group of formula:

R⁴ is hydrogen,

R⁵ is hydrogen; halogen; azido; cyano; —S—C1-4-alkyl; —SO—C1-4-alkyl; —SO₂—C1-4-alkyl; —SONH₂; or C1-20-alkyl unsubstituted or substituted by halogen, R⁶ is hydrogen, C1-20-alkyl or halogen, R⁷ is hydrogen, C2-20-alkyl or halogen, W is C1-12-alkylene, —NH— or —NHC(=O)—, X is O, S or NH, Y is O, S, —CR¹²R¹³—, —NR¹⁴— or —C(=O)—, R⁸ is aryl or heterocycle, R⁹, R¹⁰, R¹⁰ᵃ and R¹¹ are independently selected from hydrogen, C1-4-alkyl, halogen, hydroxy or methoxycarbonyl, or R¹⁰ and R¹⁰ᵃ together form a C3-6-alkylene, R¹² is hydrogen, C1-4-alkyl, halogen or hydroxy, R¹³ is hydrogen, or CR¹²R¹³ is dioxolanyl, R¹⁴ is aryl, heterocycle or a group of formula —V—R¹⁵, V is C1-12-alkylene, R¹⁵ is aryl or heterocycle, m is 1 to 4, n is 0 or 1, and at least one of R⁵, R⁶ or R⁷ is different from hydrogen when R² is hydrogen, R³ is H or 2,6-diisopropylphenyl, and R³ᵃ is H.

In another embodiment, the present invention concerns the synthesis intermediates of formula VI or stereoisomeric forms thereof,

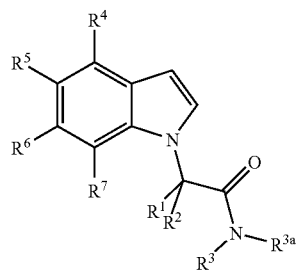

(VI)

wherein
R¹ is hydrogen,
R² is hydrogen or C1-20-alkyl,
R³ is hydrogen, C1-20-alkyl, C4-8-cycloalkyl, C5-8-cycloalkenyl, aryl, aromatic or non aromatic heterocycle, C1-20-alkoxy, or a group of formula —W—R⁸,
R³ᵃ is hydrogen, C1-20-alkyl or a group of formula:

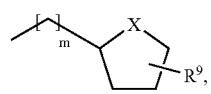

or NR³R³ᵃ is a group of formula:

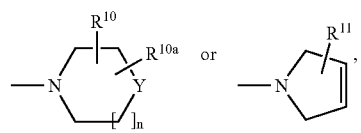

R⁴ is hydrogen,
R⁵ is hydrogen; halogen; or C1-20-alkyl unsubstituted or substituted by halogen,
R⁶ is hydrogen, C1-20-alkyl or halogen,
R⁷ is hydrogen, C2-20-alkyl or halogen,
W is C1-12-alkylene, —NH— or —NHC(=O)—,
X is O, S or NH,
Y is O, S, —CR¹²R¹³—, —NR¹⁴— or —C(=O)—,
R⁸ is aryl or heterocycle,
R⁹, R¹⁰, R¹⁰ᵃ and R¹¹ are independently selected from hydrogen, C1-4-alkyl, halogen, hydroxy or methoxycarbonyl, or R¹⁰ and R¹⁰ᵃ together form a C3-6-alkylene,
R¹² is hydrogen, C1-4-alkyl, halogen or hydroxy,
R¹³ is hydrogen,
or CR¹²R¹³ is dioxolanyl,
R¹⁴ is aryl, heterocycle or a group of formula —V—R¹⁵,
V is C1-12-alkylene,
R¹⁵ is aryl or heterocycle,
m is 1 to 4,
n is 0 or 1,
and at least one of R⁵, R⁶ or R⁷ is different from hydrogen when R² is hydrogen, R³ is H or 2,6-diisopropylphenyl, and R³ᵃ is H.

Preferably, the synthesis intermediates of formula VI are selected from the group consisting of: 2-(5-chloro-1H-indol-1-yl)propanamide; 2-(7-chloro-1H-indol-1-yl)acetamide; 2-(6-chloro-1H-indol-1-yl)acetamide, 2-(5-chloro-1H-indol-1-yl)butanamide; 2-(5-methyl-1H-indol-1-yl)propanamide; 2-(5-bromo-1H-indol-1-yl)propanamide; 2-(7-fluoro-1H-indol-1-yl)acetamide; 2-(5-bromo-1H-indol-1-yl)acetamide; 2-(5-fluoro-1H-indol-1-yl)acetamide; and 2-(5-chloro-1H-indol-1-yl)acetamide.

In one embodiment, the present invention concerns also the synthesis intermediates of formula IX or stereoisomeric forms thereof,

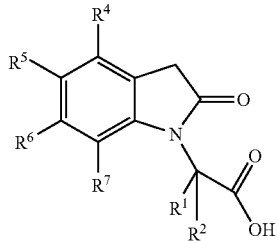

(IX)

wherein
R¹ is hydrogen,
R² is hydrogen or C1-20-alkyl,
R⁴ is hydrogen,
R⁵ is hydrogen; nitro; halogen; azido; cyano; —S—C1-4-alkyl; —SO—C1-4-alkyl; —SO₂—C1-4-alkyl; —SONH₂; C1-20-alkyl unsubstituted or substituted by halogen; or C1-20-alkoxy unsubstituted or substituted by halogen,
R⁶ is hydrogen, C1-20-alkyl or halogen,
R⁷ is hydrogen, C1-20-alkyl or halogen,
and at least one of R⁵, R⁶ or R⁷ is different from hydrogen when R² is hydrogen, R³ is H or 2,6-diisopropylphenyl, and R³ᵃ is H.

In another embodiment, the present invention concerns the synthesis intermediates of formula IX or stereoisomeric forms thereof,

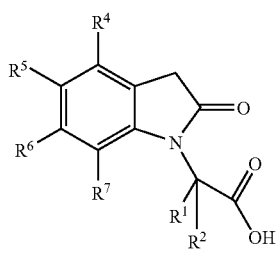

(IX)

wherein
R¹ is hydrogen,
R² is hydrogen or C1-20-alkyl,
R⁴ is hydrogen,
R⁵ is hydrogen; nitro; halogen; C1-20-alkyl unsubstituted or substituted by halogen; or C1-20-alkoxy unsubstituted or substituted by halogen,
R⁶ is hydrogen, C1-20-alkyl or halogen,
R⁷ is hydrogen, C1-20-alkyl or halogen,
and at least one of R⁵, R⁶ or R⁷ is different from hydrogen when R² is hydrogen, R³ is H or 2,6-diisopropylphenyl, and R³ᵃ is H.

Preferably, the synthesis intermediate of formula IX is (5-chloro-2-oxo-2,3-dihydro-1H-indol-1-yl)acetic acid.

The present invention also concerns the synthesis intermediates 2-(7-fluoro-2-oxo-2,3-dihydro-1H-indol-1-yl)acetamide and ethyl (5-chloro-2-oxo-2,3-dihydro-1H-indol-1-yl)acetate.

It has now been found that compounds of formula I and their pharmaceutically acceptable salts are useful in a variety of pharmaceutical indications.

For example, the compounds according to the invention are useful for the treatment of epilepsy, epileptogenesis, seizure disorders and convulsions.

These compounds may also be used for the treatment of Parkinson's disease.

These compounds may also be used for the treatment of dyskinesia induced by dopamine replacement therapy, tardive dyskinesia induced by administration of neuroleptic drugs or Huntington Chorea.

In addition, the compounds according to the invention may also be used for treating other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless leg syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

Thus, the present invention also concerns a compound having the formula I or a pharmaceutically acceptable salt thereof or stereoisomeric forms thereof as defined above for use as a medicament.

In a further aspect, the present invention concerns also the use of a compound of formula I or a pharmaceutically acceptable salt thereof for the manufacture of a medicament for the treatment of neurological and other disorders such as mentioned above.

In particular, the present invention concerns the use of a compound of formula I or a pharmaceutically acceptable salt thereof for the manufacture of a medicament for the treatment of epilepsy, Parkinson's disease, dyskinesia, migraine, bipolar disorders, chronic pain, neuropathic pain, or bronchial, asthmatic or allergic conditions.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 3 to 3000 mg, preferably 25 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a chronic neurologic condition characterised by unprovoked, recurrent epileptic seizures. An epileptic seizure is the manifestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

The term "Parkinsonian symptoms" relates to a syndrome characterized by slowness of movement (bradykinesia), rigidity and/or tremor. Parkinsonian symptoms are seen in a variety of conditions, most commonly in idiopathic Parkinsonism (i.e. Parkinson's Disease) but also following treatment of schizophrenia, exposure to toxins/drugs and head injury. It is widely appreciated that the primary pathology underlying Parkinson's disease is degeneration, in the brain, of the dopaminergic projection from the substantia nigra to the striatum. This has led to the widespread use of dopamine-replacing agents (e.g. L-3,4-dihydroxyphenylalanine (L-DOPA) and dopamine agonists) as symptomatic treatments for Parkinson's disease and such treatments have been successful in increasing the quality of life of patients suffering from Parkinson's disease. However, dopamine-replacement treatments do have limitations, especially following long-term treatment. Problems can include a wearing-off of the anti-parkinsonian efficacy of the treatment and the appearance of a range of side-effects which manifest as abnormal involuntary movements, such as dyskinesias.

The term "dyskinesia" is defined as the development in a subject of abnormal involuntary movements. This appears in patients with Huntington's disease, in Parkinson's disease patients exposed to chronic dopamine replacement therapy, and in Schizophrenia patients exposed to chronic treatment with neuroleptics. Dyskinesias, as a whole, are characterised by the development in a subject of abnormal involuntary movements. One way in which dyskinesias may arise is as a side effect of dopamine replacement therapy for parkinsonism or other basal ganglia-related movement disorders.

The term "migraine" as used herein means a disorder characterised by recurrent attacks of headache that vary widely in intensity, frequency, and duration. The attacks are commonly unilateral and are usually associated with anorexia, nausea, vomiting, phonophobia, and/or photophobia. In some cases they are preceded by, or associated with, neurological and mood disturbances. Migraine headache may last from 4 hours to about 72 hours. The International Headache Society (IHS, 1988) classifies migraine with aura (classical migraine) and migraine without aura (common migraine) as the major types of migraine. Migraine with aura consists of a headache phase preceded by characteristic visual, sensory, speech, or motor symptoms. In the absence of such symptoms, the headache is called migraine without aura.

The term "bipolar disorders" as used herein refers to those disorders classified as Mood Disorders according to the Diagnostic and Statistical Manual of Mental Disorders, 4th edition (Diagnostic and Statistical Manual of Mental Disorders (DSM-IV™), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression). Bipolar disorders are separated into four main categories in the DSM-IV (bipolar I disorder, bipolar II disorder, cyclothymia, and bipolar disorders not otherwise specified).

The term "manic episode", as used herein refers to a distinct period during which there is an abnormally and persistently elevated, expansive, or irritable mood with signs of pressured speech and psychomotor agitation.

The term "hypomania", as used herein refers to a less extreme manic episode, with lower grade of severity.

The term "major depressive episode", as used herein refers to a period of at least 2 weeks during which there is either depressed mood or the loss of interest or pleasure in nearly all activities with signs of impaired concentration and psychomotor retardation.

The term "mixed episode", as used herein refers to a period of time (lasting at least 1 week) in which the criteria are met both for a manic episode and for a major depressive episode nearly every day.

The term "chronic pain" as used herein refers to the condition gradually being recognised as a disease process distinct from acute pain. Conventionally defined as pain that persists beyond the normal time of healing, pain can also be considered chronic at the point when the individual realises that the pain is going to be a persistent part of their lives for the foreseeable future. It is likely that a majority of chronic pain syndromes involves a neuropathic component, which is usually harder to treat than acute somatic pain.

The term "neuropathic pain" as used herein refers to pain due to a dysfunctional nervous system, sometimes occurring following injury to the central nervous system (central pain), but more often caused by damage to peripheral nerves (painful peripheral neuropathy). Neuropathic pain is most likely caused by neural hyperexcitation in partially damaged nerves. Several types of painful peripheral neuropathy, which may share some underlying pathogenic mechanisms, have been distinguished, such as: (1) postraumatic painful peripheral neuropathy; (2) phantom limb pain; (3) facial (trigeminal) pains; (4) postherpetic neuralgia; (5) painful diabetic neuropathy; (6) neuropathies due to cancer tumors; (7) neuropathies induced by treatment with anti-neoplastic agents; and (8) nerve damage associated with demyelinating disease, such as multiple sclerosis. In neuropathic pain, painful reactions appear in response to normally neutral stimuli (allodynia) or as exaggerated reactions to painful stimuli (hyperalgesia). Spontaneous pain, not provoked by external stimuli, also occurs in neuropathic pain, and is the most difficult form of pain to measure and treat.

The term "tics" refers to common and often disabling neurological disorders. They are frequently associated with behaviour difficulties, including obsessive-compulsive disorder, attention deficit hyperactivity disorder and impulse control. Tics are involuntary, sudden, rapid, repetitive, nonrhythmic stereotype movements or vocalizations. Tics are manifested in a variety of forms, with different durations and degrees of complexity. Simple motor tics are brief rapid movements that often involve only one muscle group. Complex motor tics are abrupt movements that involve either a cluster of simple movements or a more coordinated sequence of movements. Simple vocal tics include sounds such as grunting, barking, yelping, and throat clearing. Complex vocal tics include syllables, phrases, repeating other people's words and repeating one's own words.

The term "tremor" refers to an involuntary, rhythmical, oscillatory movement of a body part. Tremor can be phenomenologically defined as tremor at rest or associated with an action. Such an action can be postural (maintenance of a limb position), kinetic (movement-related), or intentional (at the end of a purposeful movement). Etiologically, tremor most often occurs in Parkinson's disease (Parkinsonian rest tremor) and in essential tremor (postural and kinetic tremor), which consists of hereditary and age-related forms. Tremor may also occur in dystonia and in multiple sclerosis. Other tremors, which can arise from various etiologies, are cerebellar (intentional tremor) and Holmes' midbrain tremor (postural tremor). Tremor can also be an exaggerated form of normal physiological tremor. Apart from the behavioral context in which tremor occurs, tremor frequency is an important criterion to distinguish between various forms of tremor. Essential tremor has the highest incidence of all tremors. As it is age-related, it can be expected to increase in aging populations. Animal model and clinical data indicate that essential tremor may be primarily based on a brainstem (inferior olivary nucleus)—cerebellar dysfunction, whereas Parkinsonian tremor probably originates from abnormal activity within the basal ganglia. Excessive synchronization and/or hyperexcitation in neuronal circuits may underlie tremor activity.

The activity of the compounds of formula I, or their pharmaceutically acceptable salts, as anticonvulsants can be determined in the audiogenic seizures model. The objective of this test is to evaluate the anticonvulsant potential of a compound by means of audiogenic seizures induced in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, p. 145-181; Buchhalter J. R., Epilepsia (1993), 34, S31-S41). Results obtained with compounds of formula I are indicative of a strong pharmacological effect.

Another assay indicative of potential anticonvulsant activity is binding to levetiracetam binding site (LBS) as hereinafter described.

Activity in any of the above-mentioned indications can of course be determined by carrying out suitable clinical trials in a manner known to a person skilled in the relevant art for the particular indication and/or in the design of clinical trials in general.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally or parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

In accordance with the invention it has also been found that the compounds of formula I or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenytoin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

Of particular interest in accordance with the present invention are combinations of at least one compound of formula I or a pharmaceutically acceptable salt thereof and at least one compound inducing neural inhibition mediated by $GABA_A$ receptors. The compounds of formula I exhibit a potentiating effect on the compounds inducing neural inhibition mediated by $GABA_A$ receptors enabling, in many cases, effective treatment of conditions and disorders under reduced risk of adverse effects.

Examples of compounds inducing neural inhibition mediated by $GABA_A$ receptors include the following: benzodiazepines, barbiturates, steroids, and anticonvulsants such as valproate, viagabatrine, tiagabine or pharmaceutical acceptable salts thereof.

Benzodiazepines include the 1,4-benzodiazepines, such as diazepam and clonazepam, and the 1,5-benzodiazepines, such as clobazam. Preferred compound is clonazepam.

Barbiturates include phenobarbital and pentobarbital. Preferred compound is phenobarbital.

Steroids include adrenocorticotropic hormones such as tetracosactide acetate, etc.

Anticonvulsants include hydantoins (phenytoin, ethotoin, etc.), oxazolidines (trimethadione, etc.), succinimides (ethosuximide, etc.), phenacemides (phenacemide, acetylphenetride, etc.), sulfonamides (sulthiame, acetoazolamide, etc.), aminobutyric acids (e.g. gamma-amino-beta-hydroxybutyric acid, etc.), sodium valproate and derivatives, carbamazepine and so on.

Preferred compounds include valproic acid, valpromide, valproate pivoxil, sodium valproate, semi-sodium valproate, divalproex, clonazepam, phenobarbital, vigabatrine, tiagabine and amantadine.

Of particular interest in accordance with the present invention are combinations of at least one compound of formula I or a pharmaceutically acceptable salt thereof and at least one compound modulating neurotransmission mediated by glutamate receptors. The compounds of formula I exhibit a potentiating effect on the compounds modulating neurotransmission mediated by glutamate receptors enabling, in many cases, effective treatment of conditions and disorders under reduced risk of adverse effects.

Examples of compounds modulating neurotransmission mediated by glutamate receptors include the following: NBQX and MK-801 or pharmaceutical acceptable salts thereof.

For the preferred oral compositions, the daily dosage is in the range 3 to 3000 milligrams (mg) of compounds of formula I.

In compositions for parenteral administration, the quantity of compound of formula I present is at least 0.5% by weight and can be up to 33% by weight with respect to the total weight of the composition. For the preferred parenteral compositions, the dosage unit is in the range 3 mg to 3000 mg of compounds of formula I.

The daily dose can fall within a wide range of dosage units of compound of formula I and is generally in the range 3 to 3000 mg. However, it should be understood that the specific doses can be adapted to particular cases depending on the individual requirements, at the physician's discretion.

The LBS binding compounds provided by this invention and labelled derivatives thereof may be useful as standards and reagents in determining the ability of tested compounds (e.g., a potential pharmaceutical) to bind to the LBS receptor.

Labelled derivatives of LBS ligands provided by this invention may also be useful as radiotracers for positron emission tomography (PET) imaging or for single photon emission computerized tomography (SPECT).

The following examples are provided for illustrative purposes.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in DMSO-$d_6$ (or CDCl$_3$) solution at a probe temperature of 313 K or 300 K and at a concentration of 20 mg/ml. The instrument is locked on the deuterium signal of DMSO-d$_6$ (or CDCl$_3$). Chemical shifts are given in ppm downfield from TMS taken as internal standard.

HPLC analyses are performed using one of the following systems:

an Agilent 1100 series HPLC system mounted with an INERTSIL ODS 3 C18, DP 5 μm, 250×4.6 mm column. The gradient runs from 100% solvent A (acetonitrile, water, H$_3$PO$_4$ (5/95/0.001, v/v/v)) to 100% solvent B (acetonitrile, water, H$_3$PO$_4$ (95/5/0.001, v/v/v)) in 6 min with a hold at 100% B of 4 min. The flow rate is set at 2.5 ml/min. The chromatography is carried out at 35° C.

a HP 1090 series HPLC system mounted with a HPLC Waters Symmetry C18, 250×4.6 mm column. The gradient runs from 100% solvent A (MeOH, water, H$_3$PO$_4$ (15/85/0.001M, v/v/M)) to 100% solvent B (MeOH, water, H$_3$PO$_4$ (85/15/0.001 M, v/v/M)) in 10 min with a hold at 100% B of 10 min. The flow rate is set at 1 ml/min. The chromatography is carried out at 40° C.

Mass Spectrometric Measurements in LC/MS Mode are Performed as Follows:

HPLC Conditions

Analyses are performed using a WATERS Alliance HPLC system mounted with an INERTSIL ODS 3, DP 5 μm, 250×4.6 mm column.

The gradient runs from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μgr/ml. API spectra (+ or −) are performed using a FINNIGAN (San Jose, Calif., USA) LCQ ion trap mass spectrometer. APCI source operates at 450° C. and the capillary heater at 160° C. ESI source operates at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Mass spectrometric measurements on a TSQ 700 tandem quadrupole mass spectrometer (Finnigan MAT, San Jose, Calif., USA) in GC/MS mode are performed with a gas chromatograph model 3400 (Varian, Walnut Creek, Calif., USA) fitted with a split/splitless injector and a DB-5MS fused-silica column (15 m×0.25 mm I.D., 1 μm) from J&W Scientific (Folsom, Calif., USA). Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C.

Specific rotation is recorded on a Perkin-Elmer 341 polarimeter. The angle of rotation is recorded at 25° C. on 1% solutions in MeOH. For some molecules, the solvent is CH$_2$Cl$_2$ or DMSO, due to solubility problems.

Melting points are determined on a Büchi 535 or 545 Tottoli-type fusionometre, and are not corrected, or by the onset temperature on a Perkin Elmer DSC 7.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures.

Preparative Chiral Chromatographic separations are performed on a DAICEL Chiralpak AD 20 μm, 100*500 mm column using an in-house build instrument with various mixtures of lower alcohols and C5 to C8 linear, branched or cyclic alkanes at ±350 ml/min. Solvent mixtures as described in individual procedures.

The following abbreviations are used in the examples:

| | |
|---|---|
| AcOEt | Ethyl acetate |
| CH$_3$CN | Acetonitrile |
| DMF | N,N-Dimethylformamide |
| NBS | N-bromosuccinimide |
| NCS | N-chlorosuccinimide |
| NIS | N-iodosuccinimide |
| TFA | Trifluoroacetic acid |
| THF | Tetrahydrofuran |

In the tables, the stereochemical information is contained in the two columns headed "configuration". The second column indicates whether a compound has no stereogenic center (achiral), is a pure enantiomer (pure), a racemate (rac) or is a mixture of two stereoisomers, possibly in unequal proportions (MIXT). The first column contains the stereochemical assignment for the recognised center, following the IUPAC numbering used in the "IUPAC name" column. A number alone indicates the existence of both configurations at that center. A number followed by 'R' or 'S' indicates the known absolute configuration at that center. A number followed by '§' indicates the existence of only one but unknown absolute configuration at that center. The letter (A, B) in front is a way of distinguishing the various enantiomers of the same structure.

EXAMPLE 1

Synthesis of 2-(5-iodo-2-oxo-2,3-dihydro-1H-indol-1-yl)acetamide 2

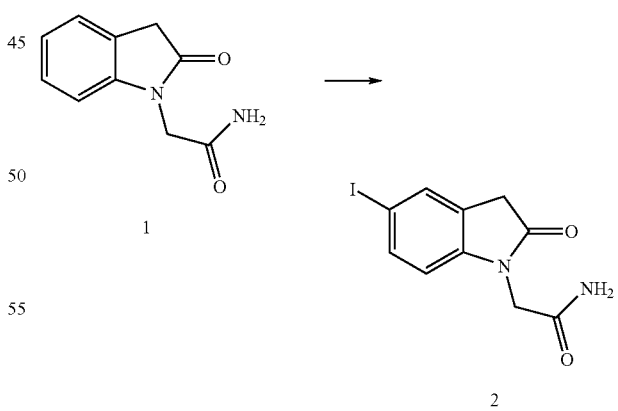

2-(2-oxo-2,3-dihydro-1H-indol-1-yl)acetamide 1 is synthesized according to the method described by Valenta et al. (Valenta, V.; Holubeck, J.; Svatek, E.; Valchar, M.; Krejci, I.; Protiva, M.; Collect. Czech. Chem. Commun. (1990), 55, 2756-2764).

Oxindole 1 (1 g, 5.25 mmol) was dissolved in CH$_3$CN (20 ml). After addition of the NIS (1.3 g, 5.78 mmol), the TFA (217 μl, 1.57 mmol) was added and the reaction was allowed at room temperature for 16 h. After evaporation of the solvent, the mixture was triturated in a 10% aqueous solution of $Na_2S_2O_3$. The beige solid formed was filtered, washed with water and with ether. After cristallization from 90% aqueous EtOH, and re-cristallization from acetonitrile, 2-(5-iodo-2-oxo-2,3-dihydro-1H-indol-1-yl)acetamide 2 was obtained as a white solid.

Yield: 166 mg (10%). MS (GC-MS, $M^+$.): 316.

EXAMPLE 2

Synthesis of 2-(5-chloro-2-oxo-2,3-dihydro-1H-indol-1-yl)acetamide 3

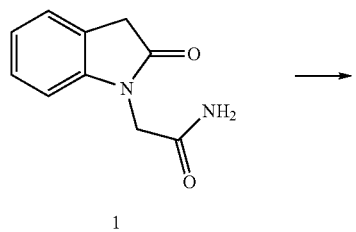

1

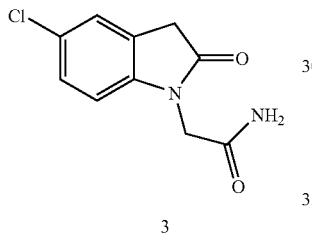

3

Oxindole 1 (1.77 g, 9.3 mmol) was dissolved in 90% $H_2SO_4$ (6 ml) at room temperature, and NCS (1.24 g, 9.3 mmol) was slowly added with stirring. After 2 hours, the mixture was poured into cold water. The precipitate was collected, washed several times with water and then with $Et_2O$. After cristallization from EtOH, 2-(5-chloro-2-oxo-2,3-dihydro-1H-indol-1-yl)acetamide 3 was obtained as a white solid.

Yield: 479 mg (23%). MS (LC-MS, $MH^+$): 225/227. MP: 226° C.

EXAMPLE 3

Synthesis of 2-(5,7-dibromo-2-oxo-2,3-dihydro-1H-indol-1-yl)acetamide 4

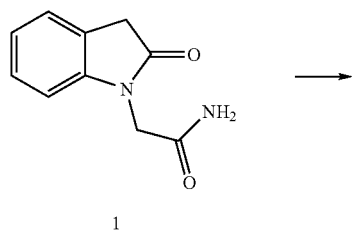

1

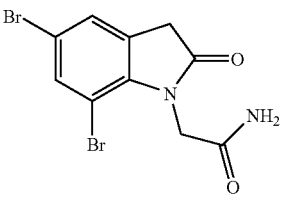

4

2-(5,7-dibromo-2-oxo-2,3-dihydro-1H-indol-1-yl)acetamide 4 was obtained as described in example 1 by using 2 equivalents of NBS. The crude material was purified by silica gel chromatography.

Yield: 129 mg (10%). MS (LC-MS, $MH^+$): 259/261.

EXAMPLE 4

Synthesis of 2-(5-nitro-2-oxo-2,3-dihydro-1H-indol-1-yl)acetamide 5

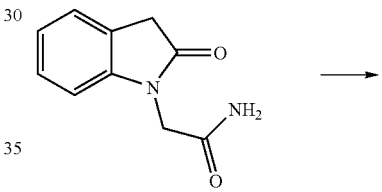

1

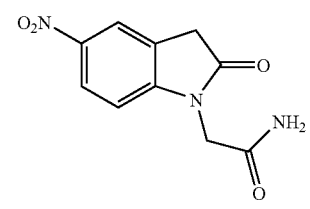

5

To a stirred solution of 2-(2-oxo-2,3-dihydro-1H-indol-1-yl)acetamide 1 (400 mg, 2.1 mmol) in TFA (20 ml) was added fuming nitric acid (170 μl, 2.7 mmol) over 10 minutes. Following addition, the ice bath was removed and the mixture was stirred at room temperature for 5 minutes, then poured carefully into ice water. The precipitate was collected, washed with water until pH 7 and dried to give a crude solid. Cristallization in a mixture acetonitrile/MeOH afforded the 2-(5-nitro-2-oxo-2,3-dihydro-1H-indol-1-yl)acetamide 5 as a green-gray solid.

Yield: 150 mg (30%).

MS (DIP, $M^+$): 235.

EXAMPLE 5

Synthesis of 2-(5-methyl-2-oxo-2,3-dihydro-1H-indol-1-yl)acetamide 24

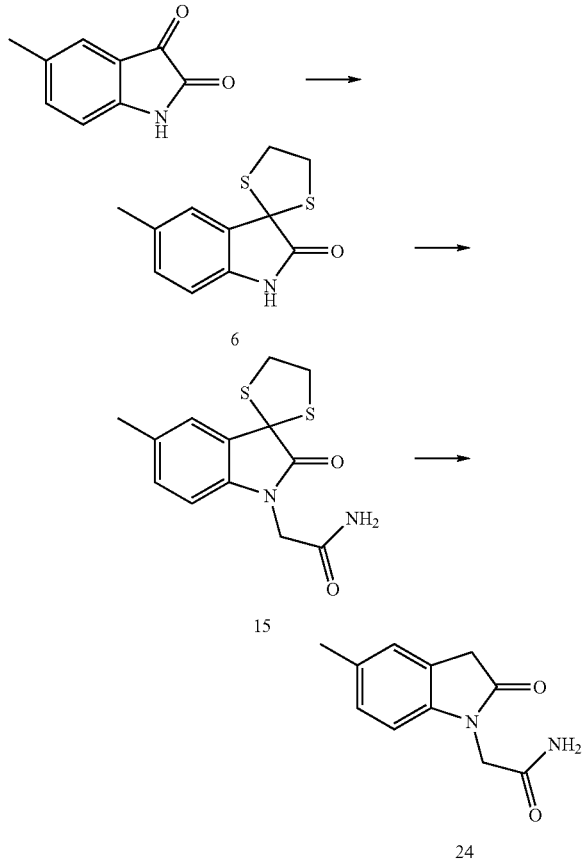

5.1 Synthesis of 5'-methylspiro[1,3-dithiolane-2,3'-indol]-2'(1'H)-one 6

5-methyl-1H-indole-2,3-dione (6 g, 37 mmol) was suspended in 100 ml of AcOH. The heterogenous mixture was heated at 60° C. After complete solubilisation, 1,2-ethanedithiol (3.15 ml, 37 mmol) was added and then neat $BF_3 \cdot OEt_2$ (9.5 ml, 75 mmol) was added dropwise. The reaction was stirred for 25 minutes, in which time the reaction mixture became homogenous. After 20 minutes at room temperature, the reaction was quenched by addition of water, the solid washed several times with large amounts of water and air dried affording 5'-methylspiro[1,3-dithiolane-2,3'-indol]-2'(1'H)-one 6 as a brown solid.

Yield: 8.65 g (98%).

MS (DIP, $M^+$): 237.

Compounds listed in table 1 can be synthesised according to the same method.

TABLE 1

| No | IUPAC NAME |
|---|---|
| 6 | 5'-methylspiro[1,3-dithiolane-2,3'-indol]-2'(1'H)-one |
| 7 | 5'-[(trifluoromethyl)oxy]spiro[1,3-dithiolane-2,3'-indol]-2'(1'H)-one |
| 8 | 5'-(1-methylethyl)spiro[1,3-dithiolane-2,3'-indol]-2'(1'H)-one |
| 9 | 5'-ethylspiro[1,3-dithiolane-2,3'-indol]-2'(1'H)-one |
| 10 | 5'-fluorospiro[1,3-dithiolane-2,3'-indol]-2'(1'H)-one |
| 11 | 5',7'-dimethylspiro[1,3-dithiolane-2,3'-indol]-2'(1'H)-one |
| 12 | 5'-propylspiro[1,3-dithiolane-2,3'-indol]-2'(1'H)-one |
| 13 | 5'-(trifluoromethyl)spiro[1,3-dithiolane-2,3'-indol]-2'(1'H)-one |
| 14 | 5',6'-dimethylspiro[1,3-dithiolane-2,3'-indol]-2'(1'H)-one |

5.2 Synthesis of 2-[5'-methyl-2'-oxospiro[1,3-dithiolane-2,3'-indol]-1'(2'H)-yl]acetamide 15

Compound 6 (8 g, 33.7 mmol) was dissolved in dry DMF (80 ml) under a nitrogen atmosphere. The solution was cooled at 0° C. and NaH (1.62 g, 37.13 mmol, 60% dispersion) was carefully added portionwise. When the nitrogen evolution ceased, bromoacetamide (5.6 g, 37.13 mmol) was added. After 30 minutes, the mixture was poured into cold water and the solid filtered off, washed with water and hexane. The crude material was directly crystallized in acetonitrile affording 2-[5'-methyl-2'-oxospiro[1,3-dithiolane-2,3'-indol]-1'(2'H)-yl]acetamide 15 as a white solid.

Yield: 4.86 g (49%).

MS (LC-MS, $MH^+$): 295.

Compounds listed in table 2 can be synthesised according to the same method.

TABLE 2

| No | IUPAC NAME |
|---|---|
| 15 | 2-(5'-methyl-2'-oxospiro[1,3-dithiolane-2,3'-indol]-1'(2'H)-yl)acetamide |
| 16 | 2-[2'-oxo-5'-[(trifluoromethyl)oxy]spiro[1,3-dithiolane-2,3'-indol]-1'(2'H)-yl]acetamide |
| 17 | 2-[5'-(1-methylethyl)-2'-oxospiro[1,3-dithiolane-2,3'-indol]-1'(2'H)-yl]acetamide |
| 18 | 2-(5'-ethyl-2'-oxospiro[1,3-dithiolane-2,3'-indol]-1'(2'H)-yl)acetamide |
| 19 | 2-(5'-fluoro-2'-oxospiro[1,3-dithiolane-2,3'-indol]-1'(2'H)-yl)acetamide |
| 20 | 2-(5',7'-dimethyl-2'-oxospiro[1,3-dithiolane-2,3'-indol]-1'(2'H)-yl)acetamide |
| 21 | 2-(2'-oxo-5'-propylspiro[1,3-dithiolane-2,3'-indol]-1'(2'H)-yl)acetamide |
| 22 | 2-[2'-oxo-5'-(trifluoromethyl)spiro[1,3-dithiolane-2,3'-indol]-1'(2'H)-yl]acetamide |
| 23 | 2-(5',6'-dimethyl-2'-oxospiro[1,3-dithiolane-2,3'-indol]-1'(2'H)-yl)acetamide |

5.3 Synthesis of 2-5-methyl-2'-oxo-2,3-dihydro-1H-indol-1-yl)acetamide 24

The Raney Nickel was prepared as an aqueous slurry after removing four fifth of water of the commercial solution. Aqueous Raney nickel (10 ml) was added to a solution of compound 15 (4.06 g, 13.8 mmol) in 40 ml of distilled THF and the mixture was further vigourously stirred at room temperature. When no starting material was detected by thin layer chromatography, the mixture was diluted with THF and filtered through a Celite pad. After removal of the solvent, the crude material was purified by silica gel chromatography ($CH_2Cl_2$/MeOH 95/5 then 90/10), and the solvent was evaporated to yield the 2-(5-methyl-2-oxo-2,3-dihydro-1H-indol-1-yl)acetamide 24 as a white solid.

Yield: 697 mg (21%).

MS (LC-MS, $MH^+$): 205.

EXAMPLE 6

Synthesis of 2-(5-chloro-2-oxo-2,3-dihydro-1H-indol-1-yl)propanamide 32, 33 and 34

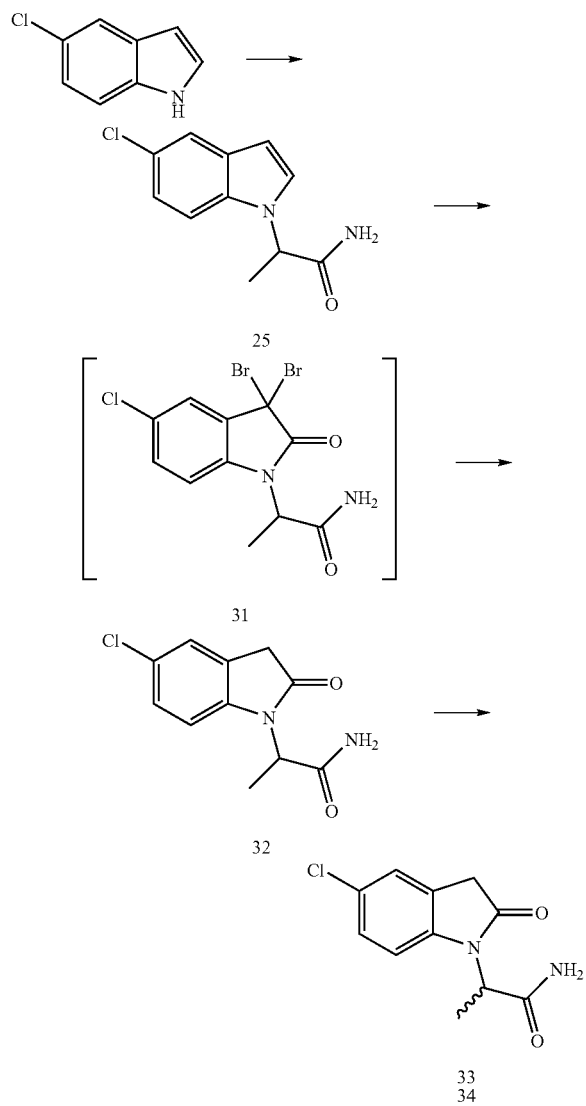

6.1 Synthesis of 2-(5-chloro-1H-indol-1-yl)propanamide 25

A dispersion of 60% NaH (6.85 g, 0.17 mol) was added to an ice-cooled solution of 5-chloroindole (20 g, 0.13 mol) in 250 ml of dry DMF. The stirring was continued for 20 minutes at room temperature, and the mixture was cooled again with an ice bath. After portionwise addition of solid 2-bromopropanamide (24.1 g, 0.15 mol), the reaction mixture was stirred for 1 h 30 at room temperature, then poured into cold water and extracted 3 times with AcOEt. The combined organic phases were dried over $Na_2SO_4$, filtered and concentrated in vacuo. The crude material was purified by silica gel chromatography (AcOEt/hexane 50/50) to give pure 2-(5-chloro-1H-indol-1-yl)propanamide 25 as a white solid.

Yield: 13.45 g (46%).

MS (LC-MS, $MH^+$): 223/225.

Compounds listed in table 3 can be synthesised according to the same method.

TABLE 3

| No | Configuration | IUPAC NAME |
|---|---|---|
| 25 | 2 rac | 2-(5-chloro-1H-indol-1-yl)propanamide |
| 26 | achiral | 2-(7-chloro-1H-indol-1-yl)acetamide |
| 27 | achiral | 2-(6-chloro-1H-indol-1-yl)acetamide |
| 28 | 2 rac | 2-(5-chloro-1H-indol-1-yl)butanamide |
| 29 | 2 rac | 2-(5-methyl-1H-indol-1-y)propanamide |
| 30 | 2 rac | 2-(5-bromo-1H-indol-1-yl)propanamide |
| 55 | achiral | 2-(7-fluoro-1H-indol-1-yl)acetamide |
| 112 | achiral | 2-(5-bromo-1H-indol-1-yl)acetamide |
| 113 | achiral | 2-(5-fluoro-1H-indol-1-yl)acetamide |
| 114 | achiral | 2-(5-chloro-1H-indol-1-yl)acetamide |

6.2 Synthesis of 2-(5-chloro-2-oxo-2,3-dihydro-1H-indol-1-yl)propanamide 32

Pyridinium bromide perbromide (38.8 g, 117 mmol) was added in portions over a period of 30 minutes to a stirred solution of 2-(5-chloro-1H-indol-1-yl)propanamide 25 (13 g, 58.4 mmol) in tert-butanol (100 ml) at room temperature. The reaction mixture was stirred for 30 minutes, then poured into water and diluted with AcOEt. After removal of the organic layer, the aqueous phase was extracted twice with AcOEt. Combined organic phases were dried over $Na_2SO_4$ and concentrated. 2-(3,3-dibromo-5-chloro-2-oxo-2,3-dihydro-1H-indol-1-yl)propanamide 31 was obtained as a crude oil and was directly used in the next step, without further purification.

Zinc dust (23.71 g, 0.58 mol) was added to a stirred solution of compound 31 (theoretical: 58.4 mmol) in AcOH (110 ml) at 0° C. After 1 hour, the reaction mixture was filtered through a Celite pad. The filtrate was diluted with AcOEt and cold water. The pH was adjusted to 7 and the layers were separated. The aqueous phase was extracted again with AcOEt. Organic layers were dried over $Na_2SO_4$ and concentrated. The beige solid was cristallized in AcOEt and afforded 2-(5-chloro-2-oxo-2,3-dihydro-1H-indol-1-yl)propanamide 32 as a white solid.

Yield: 2.5 g (18%).

MS (LC-MS, $MH^+$): 239/241.

Compound 32 (2.5 g, 10.5 mmol) was resolved into its enantiomers by chiral chromatography (DAICEL, Chiralcel OD phase, eluent: 50/50 ethanol/hexane) to afford enantiomers 33 (first eluted) and 34 (second eluted) as white solids.

Compound 33:

Yield: 977 mg (39%).

MS (LC-MS, $MH^+$): 239/241.

MP: 171-172° C.

Compound 34:

Yield: 941 mg (37%).

MS (LC-MS, $MH^+$): 239/241.

MP: 171-172° C.

EXAMPLE 7

Synthesis of N-(4-tert-Butyl-phenyl)-2-(5-chloro-2-oxo-2,3-dihydro-indol-1-yl)-acetamide 85

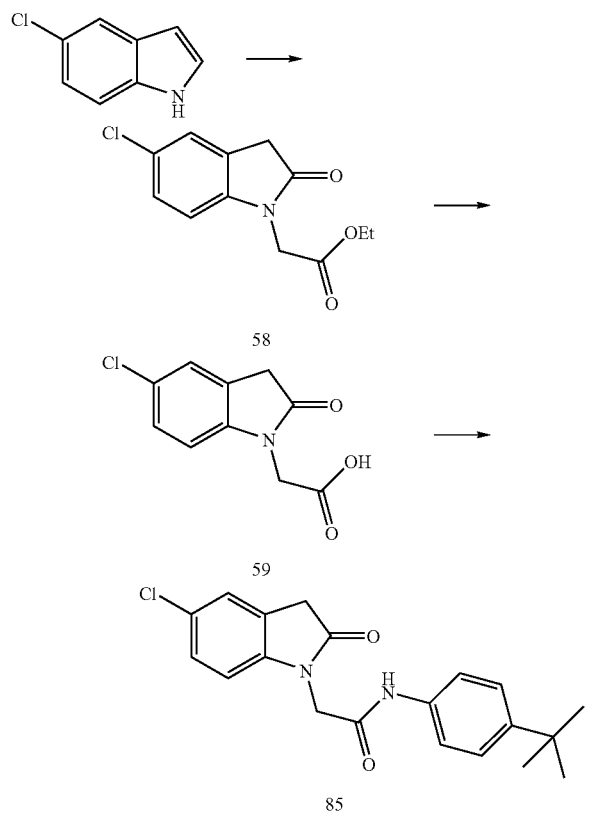

7.1 Synthesis of ethyl(5-chloro-2-oxo-2,3-dihydro-1H-indol-1-yl)acetate 58

The ester 58 was obtained from 5-chloroindole and ethyl bromoacetate (instead of bromo-acetamide) using the methodology described in example 6.

MS (GC-MS, $M^+$.): 253/255.

7.2 Synthesis of (5-chloro-2-oxo-2,3-dihydro-1H-indol-1-yl)acetic acid 59

In a two neck flask, ethyl (5-chloro-2-oxo-2,3-dihydro-1H-indol-1-yl)acetate 58 (0.1 g, 0.39 mmol) was stirred overnight at room temperature in aqueous HCl (6 M, 2 ml) and warmed at 80° C. until disappearance of the starting material by TLC. The reaction mixture was cooled down to room temperature, filtered and the filtrate was washed by cold water to afford (5-chloro-2-oxo-2,3-dihydro-1H-indol-1-yl)acetic acid 59 (74 mg).

LC/MS: 225/227 ($MH^+$).

7.3 Synthesis of N-(4tert-Butyl-phenyl)-2-(5-chloro-2-oxo-2,3-dihydro-indol-1-yl)-acetamide 85

In a 1 ml polypropylene vial, 300 µl of a 0.15 M stock solution of (5-chloro-2-oxo-2,3-dihydro-1H-indol-1-yl)acetic acid 59 in a 1/1 $CH_2Cl_2$/DMF mixture were added onto N-dicyclohexyl-N-methyl polystyrene (from Novabiochem, loading: 1.9 mmol/g, 35 mg) and N,N-diisopropyl-methylpolystyrene (from Argonaut, loading: 3.49 mmol/g, 25.4 mg) followed by 4tertbutyl-aniline (0.044 mmol, 6.6 mg). The reaction mixture was stirred 40 h under vortex and quenched with DMF (400 µl). The suspension was allowed to sediment and the liquid was concentrated under vacuo to afford N-(4-tert-butyl-phenyl)-2-(5-chloro-2-oxo-2,3-dihydro-indol-1-yl)-acetamide 85 (10 mg).

MS (LC-MS, $MH^+$): 357/359.

Compounds described in table 4 may be prepared according to one of the previous methods.

The synthesis intermediate 2-(7-fluoro-2-oxo-2,3-dihydro-1H-indol-1-yl)acetamide may also be prepared according to one of the previous methods.

TABLE 4

Compounds of formula I.

| No | Configuration | | IUPAC NAME | MS (LC-MS, $MH^+$) | $α_D$ (MeOH, 25° C., 1%) |
|---|---|---|---|---|---|
| 2 | | achiral | 2-(5-iodo-2-oxo-2,3-dihydro-1H-indol-1-yl)acetamide | 316 (GC-MS, $M^{+\cdot}$) | |
| 3 | | achiral | 2-(5-chloro-2,3-dihydro-1H-indol-1-yl)acetamide | 225/227 | |
| 4 | | achiral | 2-(5,7-dibromo-2-oxo-2,3-dihydro-1H-indol-1-yl)acetamide | 347/349/351 | |
| 5 | | achiral | 2-(5-nitro-2-oxo-2,3-dihydro-1H-indol-1-yl)acetamide | 235 (DIP, $M^+$) | |
| 24 | | achiral | 2-(5-methyl-2-oxo-2,3-dihydro-1H-indol-1-yl)acetamide | 205 | |
| 32 | 2 | rac | 2-(5-chloro-2-oxo-2,3-dihydro-1H-indol-1-yl)propanamide | 239/241 | |
| 33 | 2R | pure | (2R)-2-(5-chloro-2-oxo-2,3-dihydro-1H-indol-1-yl)propanamide | 239/241 | +64.55 |
| 34 | 2S | pure | (2S)-2-(5-chloro-2-oxo-2,3-dihydro-1H-indol-1-yl)propanamide | 239/241 | −60.82 |
| 35 | | achiral | 2-[2-oxo-5-(trifluoromethoxy)-2,3-dihydro-1H-indol-1-yl]acetamide | 275 | |
| 36 | | achiral | 2-(5-isopropyl-2-oxo-2,3-dihydro-1H-indol-1-yl)acetamide | 233 | |
| 37 | | achiral | 2-(5-ethyl-2-oxo-2,3-dihydro-1H-indol-1-yl)acetamide | 219 | |
| 38 | | achiral | 2-(5-fluoro-2-oxo-2,3-dihydro-1H-indol-1-yl)acetamide | 209 | |
| 39 | | achiral | 2-(5,7-dimethyl-2-oxo-2,3-dihydro-1H-indol-1-yl)acetamide | 219 | |
| 40 | | achiral | 2-(5-bromo-2-oxo-2,3-dihydro-1H-indol-1-yl)acetamide | 269/271 | |
| 41 | | achiral | 2-(2-oxo-5-propyl-2,3-dihydro-1H-indol-1-yl)acetamide | 233 | |
| 42 | | achiral | 2-[2-oxo-5-(trifluorormethyl)-2,3-dihydro-1H-indol-1-yl]acetamide | 259 | |
| 43 | | achiral | 2-(5,6-dimethyl-2-oxo-2,3-dihydro-1H-indol-1-yl)acetamide | 219 | |
| 44 | | achiral | 2-(7-chloro-2-oxo-2,3-dihydro-1H-indol-1-yl)acetamide | 224/226 | |
| 45 | | achiral | 2-(6-chloro-2-oxo-2,3-dihydro-1H-indol-1-yl)acetamide | 225/227 | |
| 46 | 2 | rac | 2-(5-chloro-2-oxo-2,3-dihydro-1H-indol-1-yl)butanamide | 252/254 | |
| 47 | A-2§ | pure | (+)-2-(5-chloro-2-oxo-2,3-dihydro-1H-indol-1-yl)butanamide | 252/254 | +46.23 |
| 48 | B-2§ | pure | (−)-2-(5-chloro-2-oxo-2,3-dihydro-1H-indol-1-yl)butanamide | 252/254 | −38.68 |
| 49 | 2 | rac | 2-(5-methyl-2-oxo-2,3-dihydro-1H-indol-1-yl)propanamide | 219 | |

TABLE 4-continued

Compounds of formula I.

| No | Configuration | | IUPAC NAME | MS (LC-MS, MH⁺) | α_D (MeOH, 25° C., 1%) |
|---|---|---|---|---|---|
| 50 | A-2§ | pure | (+)-2-(5-methyl-2-oxo-2,3-dihydro-1H-indol-1-yl)propanamide | 219 | +84.39 |
| 51 | B-2§ | pure | (−)-2-(5-methyl-2-oxo-2,3-dihydro-1H-indol-1-yl)propanamide | 219 | |
| 52 | 2 | rac | 2-(5-bromo-2-oxo-2,3-dihydro-1H-indol-1-yl)propanamide | 283/285 | |
| 53 | A-2§ | pure | (−)-2-(5-bromo-2-oxo-2,3-dihydro-1H-indol-1-yl)propanamide | 283/285 | −40.33 |
| 54 | B-2§ | pure | (+)-2-(5-bromo-2-oxo-2,3-dihydro-1H-indol-1-yl)propanamide | 283/285 | +44.16 |
| 57 | | achiral | 2-(5-chloro-7-fluoro-2-oxo-2,3-dihydro-1H-indol-1-yl)acetamide | 243/245 | |
| 60 | | achiral | 2-(5-chloro-2-oxo-2,3-dihydro-1H-indol-1-yl)-N-(3-hydroxyphenyl)acetamide | 317/319 | |
| 61 | | achiral | 2-(5-chloro-2-oxo-2,3-dihydro-1H-indol-1-yl)-N-(3-fluorophenyl)acetamide | 319/321 | |
| 62 | | achiral | 2-(5-chloro-2-oxo-2,3-dihydro-1H-indol-1-yl)-N-[3-(2-pyridin-2-ylethyl)phenyl]acetamide | 406/408 | |
| 63 | | achiral | 2-(5-chloro-2-oxo-2,3-dihydro-1H-indol-1-yl)-N-[6-(hydroxymethyl)cyclohex-3-en-1-yl]acetamide | 335/337 | |
| 64 | | achiral | 5-chloro-1-[2-oxo-2-(4-pyridin-2-ylpiperazin-1-yl)ethyl]-1,3-dihydro-2H-indol-2-one | 371/373 | |
| 65 | | achiral | 5-chloro-1-{2-[4-(3-methylphenyl)piperazin-1-yl]-2-oxoethyl}-1,3-dihydro-2H-indol-2-one | 384/386 | |
| 66 | | achiral | 2-(5-chloro-2-oxo-2,3-dihydro-1H-indol-1-yl)-N-(4-hydroxy-3-methoxybenzyl)acetamide | 361/363 | |
| 67 | | achiral | 2-(5-chloro-2-oxo-2,3-dihydro-1H-indol-1-yl)-N-(pyridin-4-ylmethyl)-N-(tetrahydrofuran-2-ylmethyl)acetamide | 400/402 | |
| 68 | | achiral | 5-chloro-1-[2-(3-hydroxypiperidin-1-yl)-2-oxoethyl]-1,3-dihydro-2H-indol-2-one | 309/311 | |
| 69 | | achiral | 2-(5-chloro-2-oxo-2,3-dihydro-1H-indol-1-yl)-N'-isonicotinoylacetohydrazide | 345/347 | |
| 70 | | achiral | 5-chloro-1-(2-oxo-2-thiomorpholin-4-ylethyl)-1,3-dihydro-2H-indol-2-one | 311/313 | |
| 71 | | achiral | 2-(5-chloro-2-oxo-2,3-dihydro-1H-indol-1-yl)-N-(4H-1,2,4-triazol-3-yl)acetamide | 292/294 | |
| 72 | | achiral | 2-(5-chloro-2-oxo-2,3-dihydro-1H-indol-1-yl)-N-[4-(methylsulfonyl)benzyl]acetamide | 393/395 | |
| 73 | | achiral | 1-[(-5-chloro-2-oxo-2,3-dihydro-1H-indol-1-yl)acetyl]octahydroquinolin-4(1H)-one | 361/363 | |
| 74 | | achiral | N'-(4-bromophenyl)-2-(5-chloro-2-oxo-2,3-dihydro-1H-indol-1-yl)acetohydrazide | 394/396/398 | |
| 75 | | achiral | 2-(5-chloro-2-oxo-2,3-dihydro-1H-indol-1-yl)-N-(6-methoxypyridin-3-yl)acetamide | 332/334 | |
| 76 | | achiral | N-butyl-2-(5-chloro-2-oxo-2,3-dihydro-1H-indol-1-yl)acetamide | 281/283 | |
| 77 | | achiral | 2-(5-chloro-2-oxo-2,3-dihydro-1H-indol-1-yl)-N-(3-hydroxypropyl)acetamide | 283/285 | |
| 78 | | achiral | 2-(5-chloro-2-oxo-2,3-dihydro-1H-indol-1-yl)-N-[3-(dimethylamino)propyl]acetamide | 310/312 | |
| 79 | | achiral | 5-chloro-1-{2-oxo-2-[4-(2-phenylethyl)piperazin-1-yl]ethyl}-1,3-dihydro-2H-indol-2-one | 398/400 | |
| 80 | | achiral | ethyl {[(5-chloro-2-oxo-2,3-dihydro-1H-indol-1-yl)acetyl]amino}acetate | 311/313 | |
| 81 | | achiral | 2-(5-chloro-2-oxo-2,3-dihydro-1H-indol-1-yl)-N-(3-ethoxypropyl)acetamide | 311/313 | |
| 82 | | achiral | 2-(5-chloro-2-oxo-2,3-dihydro-1H-indol-1-yl)-N-(2-fluoroethyl)acetamide | 271/273 | |
| 83 | | achiral | 2-(5-chloro-2-oxo-2,3-dihydro-1H-indol-1-yl)-N-methoxy-N-methylacetamide | 269/271 | |
| 84 | | achiral | 2-(5-chloro-2-oxo-2,3-dihydro-1H-indol-1-yl)-N-(3,4-dimethylphenyl)acetamide | 329/331 | |
| 85 | | achiral | N-(4-tert-butylphenyl)-2-(5-chloro-2-oxo-2,3-dihydro-1H-indol-1-yl)acetamide | 357/359 | |
| 86 | | achiral | 2-(5-chloro-2-oxo-2,3-dihydro-1H-indol-1-yl)-N-(3-hydroxy-2,2-dimethylpropyl)acetamide | 311/313 | |
| 87 | | achiral | 2-(5-chloro-2-oxo-2,3-dihydro-1H-indol-1-yl)-N-[1-(hydroxymethyl)propyl]acetamide | 297/299 | |
| 88 | | achiral | 2-(5-chloro-2-oxo-2,3-dihydro-1H-indol-1-yl)-N-(3,3,3-trifluoro-2-hydroxypropyl)acetamide | 337/339 | |
| 89 | | achiral | 2-(5-chloro-2-oxo-2,3-dihydro-1H-indol-1-yl)-N-(2-hydroxy-2-phenylethyl)acetamide | 345/347 | |
| 90 | | achiral | 5-chloro-1-{2-[4-(4-hydroxyphenyl)piperazin-1-yl]-2-oxoethyl}-1,3-dihydro-2H-indol-2-one | 386/388 | |
| 91 | | achiral | 2-(5-chloro-2-oxo-2,3-dihydro-1H-indol-1-yl)-N-(pyridin-4-ylmethyl)acetamide | 316/318 | |
| 92 | | achiral | 2-(5-chloro-2-oxo-2,3-dihydro-1H-indol-1-yl)-N-[(5-methyl-2-furyl)methyl]acetamide | 319/321 | |

TABLE 4-continued

Compounds of formula I.

| No | Configuration | IUPAC NAME | MS (LC-MS, MH+) | $\alpha_D$ (MeOH, 25° C., 1%) |
|---|---|---|---|---|
| 93 | achiral | 2-(5-chloro-2-oxo-2,3-dihydro-1H-indol-1-yl)-N-[3-(1H-pyrazol-1-yl)propyl]acetamide | 333/335 | |
| 94 | achiral | methyl 3-[(5-chloro-2-oxo-2,3-dihydro-1H-indol-1-yl)acetyl]-1,3-thiazolidine-4-carboxylate | 355/357 | |
| 95 | achiral | 5-chloro-1-[2-(2,5-dihydro-1H-pyrrol-1-yl)-2-oxoethyl]-1,3-dihydro-2H-indol-2-one | 277/279 | |
| 96 | achiral | 2-(5-chloro-2-oxo-2,3-dihydro-1H-indol-1-yl)-N'-(4,5-dihydro-1H-imidazol-2-yl)acetohydrazide | 308/310 | |
| 97 | achiral | 2-(5-chloro-2-oxo-2,3-dihydro-1H-indol-1-yl)-N-[2-(3,4-dimethoxyphenyl)ethyl]acetamide | 389/391 | |
| 98 | achiral | 2-(5-chloro-2-oxo-2,3-dihydro-1H-indol-1-yl)-N-[2-(2-chlorophenyl)ethyl]acetamide | 363/365/367 | |
| 99 | achiral | 2-(5-chloro-2-oxo-2,3-dihydro-1H-indol-1-yl)-N-[2-(4-methylphenyl)ethyl]acetamide | 343/345 | |
| 100 | achiral | 2-(5-chloro-2-oxo-2,3-dihydro-1H-indol-1-yl)-N-(2-morpholin-4-ylethyl)acetamide | 338/340 | |
| 101 | achiral | 2-(5-chloro-2-oxo-2,3-dihydro-1H-indol-1-yl)-N-[2-(3,4,5,6-tetrahydro-1-benzazocin-1(2H)-yl)propyl]acetamide | 426/428 | |
| 102 | achiral | 2-(5-chloro-2-oxo-2,3-dihydro-1H-indol-1-yl)-N-[2-(2-methylpiperidin-1-yl)ethyl]acetamide | 350/352 | |
| 103 | achiral | 2-(5-chloro-2-oxo-2,3-dihydro-1H-indol-1-yl)-N-(2-nitrobenzyl)acetamide | 360/362 | |
| 104 | achiral | 2-(5-chloro-2-oxo-2,3-dihydro-1H-indol-1-yl)-N-(3,4-dihydro-1H-isochromen-1-ylmethyl)acetamide | 371/373 | |
| 105 | achiral | N-(2-chloro-6-fluorobenzyl)-2-(5-chloro-2-oxo-2,3-dihydro-1H-indol-1-yl)acetamide | 367/369/371 | |
| 106 | achiral | N-benzyl-2-(5-chloro-2-oxo-2,3-dihydro-1H-indol-1-yl)-N-methylacetamide | 329/311 | |
| 107 | achiral | 2-(5-chloro-2-oxo-2,3-dihydro-1H-indol-1-yl)-N-{2-[(trifluoromethyl)thio]benzyl}acetamide | 415/417 | |
| 108 | achiral | 5-chloro-1-[2-(1,4-dioxa-8-azaspiro[4.5]dec-8-yl)-2-oxoethyl]-1,3-dihydro-2H-indol-2-one | 351/353 | |
| 109 | achiral | 2-(5-chloro-2-oxo-2,3-dihydro-1H-indol-1-yl)-N-cycloheptylacetamide | 321/323 | |
| 110 | achiral | 5-chloro-1-{2-[4-(2-morpholin-4-ylethyl)piperazin-1-yl]-2-oxoethyl}-1,3-dihydro-2H-indol-2-one | 407/409 | |
| 111 | achiral | 2-(5-chloro-2-oxo-2,3-dihydro-1H-indol-1-yl)-N-pyridin-3-ylacetamide | 302/304 | |

EXAMPLE 8

LBS Binding Assay

[LBS stands for Levetiracetam Binding Site cf. M. Noyer et al., Eur. J. Pharmacol. (1995), 286, 137-146.]

The inhibition constant ($K_i$) of a compound is determined in competitive binding experiments by measuring the binding of a single concentration of a radioactive ligand at equilibrium with various concentrations of the unlabeled test substance. The concentration of the test substance inhibiting 50% of the specific binding of the radioligand is called the $IC_{50}$. The equilibrium dissociation constant $K_i$ is proportional to the $IC_{50}$ and is calculated using the equation of Cheng and Prusoff (Cheng Y. et al., Biochem. Pharmacol. (1972), 22, 3099-3108).

The concentration range usually encompasses 6 log units with variable steps (0.3 to 0.5 log). Assays are performed in mono- or duplicate, each $K_i$ determination is performed on two different samples of test substance.

Cerebral cortex from 200-250 g male Sprague-Dawley rats are homogenised using a Potter S homogeniser (10 strokes at 1,000 rpm; Braun, Germany) in 20 mmol/l Tris-HCl (pH 7.4), 250 mmol/l sucrose (buffer A); all operations are performed at 4° C. The homogenate is centrifuged at 30,000×g for 15 min. The crude membrane pellet obtained is resuspended in 50 mmol/l Tris-HCl (pH 7.4), (buffer B) and incubated 15 min at 37° C., centrifuged at 30,000×g for 15 min and washed twice with the same buffer. The final pellet is resuspended in buffer A at a protein concentration ranging from 15 to 25 mg/ml and stored in liquid nitrogen.

Membranes (150-200 µg of protein/assay) are incubated at 4° C. for 120 min in 0.5 ml of a 50 mmol/l Tris-HCl buffer (pH 7.4) containing 2 mmol/l $MgCl_2$, $10^{-9}$ to $2.10^{-9}$ mol/l of [$^3$H]-2-[4-(3-azidophenyl)-2-oxo-1-pyrrolidinyl]butanamide and increasing concentrations of the test substance. The non specific binding (NSB) is defined as the residual binding observed in the presence of a concentration of reference substance (e.g. $10^{-3}$ mol/l levetiracetam) that binds essentially all the receptors. Membrane-bound and free radioligands are separated by rapid filtration through glass fiber filters (equivalent to Whatman GF/C or GF/B; VEL, Belgium) pre-soaked in 0.1% polyethyleneimine and $10^{-3}$ mol/l levetiracetam to reduce non specific binding. Samples and filters are rinsed by at least 6 ml of 50 mmol/l Tris-HCl (pH 7.4) buffer. The entire filtration procedure does not exceed 10 seconds per sample. The radioactivity trapped onto the filters is counted by liquid scintillation in a β-counter (Tri-Carb 1900 or TopCount 9206, Camberra Packard, Belgium, or any other equivalent counter). Data analysis is performed by a computerized non linear curve fitting method using a set of equations describing several binding models assuming populations of independent non-interacting receptors, which obey to the law of mass.

EXAMPLE 9

Animal Model of Sound-Susceptible Mice

The aim of this test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145-181; Buchhalter J. R., Epilepsia (1993), 34, S31-S41).

Male or female genetically sound-sensitive mice (14-28 g; N=10), derived from a DBA strain originally selected by Dr. Lehmann of the Laboratory of Acoustic Physiology (Paris) and bred in the UCB Pharma Sector husbandry unit since 1978, are used. The experimental design consists of several groups, one group receiving the vehicle control and the other groups different doses of the test-compound. The compounds are administered intraperitoneally 60 minutes before the induction of audiogenic seizures. The range of the doses administered has a logarithmic progression, generally between $1.0 \times 10^{-5}$ mol/kg and $1.0 \times 10^{-3}$ mol/kg, but lower or higher doses are tested if necessary.

For testing, the animals are placed in small cages, one mouse per cage, in a sound-attenuated chamber. After a period of orientation of 30 seconds, the acoustic stimulus (90 dB, 10-20 kHz) is delivered for 30 seconds via loudspeakers positioned above each cage. During this interval, the mice are observed and the presence of the 3 phases of the seizure activity namely wild running, clonic and tonic convulsions, is recorded. The proportion of mice protected against wild running, clonic and tonic convulsions, respectively, is calculated.

For active compounds, an $ED_{50}$ value, i.e. the dose producing 50% protection relative to the control group, together with 95% confidence limits, was calculated using a Probit Analysis (SAS/STAT® Software, version 6.09, PROBIT procedure) of the proportions of protected mice for each of the 3 phases of the seizure activity.

The invention claimed is:

1. A compound of the formula I or a pharmaceutically acceptable salt thereof or stereoisomeric forms thereof, (I)

wherein
$R^1$ is hydrogen,
$R^2$ is hydrogen or $C_{1-20}$-alkyl,
$R^3$ is hydrogen, $C_{1-20}$-alkyl, $C_{4-8}$-cycloalkyl, $C_{5-8}$-cycloalkylenyl, aryl, $C_{1-20}$-alkoxy, or a group of formula —W-$R^8$;
$R^{3a}$ is hydrogen or $C_{1-20}$-alkyl,
$R^4$ is hydrogen,
$R^5$ is halogen or trifluoromethyl,
$R^6$ is hydrogen, $C_{1-20}$-alkyl or halogen,
$R^7$ is hydrogen, $C_{1-20}$-alkyl or halogen,
W is $C_{1-12}$-alkylene, —NH— or —NHC(=O)—, and
$R^8$ is aryl.

2. A compound of the formula I or a pharmaceutically acceptable salt thereof or stereoisomeric forms thereof, (I)

wherein
$R^1$ is hydrogen,
$R^2$ is hydrogen or $C_{1-4}$alkyl,
$R^3$ is hydrogen; $C_{1-6}$-alkyl unsubstituted or substituted by 1 to 5 substituents selected from halogen, hydroxy, alkoxy, alkoxycarbonyl and alkylamino; $C_{5-7}$-cycloalkyl; (hydroxymethyl) cyclohexenyl; phenyl unsubstituted or substituted by 1 to 5 substituents selected from halogen, $C_{1-4}$-alkyl, hydroxy, methoxy, nitro, methylsulfonyl, and trifluoromethylthio; or a group of formula —W-$R^8$,
$R^{3a}$ is hydrogen, $C_{1-4}$-alkyl,
$R^4$ is hydrogen,
$R^5$ is halogen or triflouromethyl,
$R^6$ is hydrogen, $C_{1-6}$-alkyl or halogen,
$R^7$ is hydrogen, methyl or halogen,
W is $C_{1-4}$-alkylene unsubstituted or substituted by halogen, hydroxy, $C_{1-4}$-alkyl or alkoxy; —NH—; or —NHC(=O)—, and
$R^8$ is phenyl unsubstituted or substituted by 1 to 5 substituents selected from halogen, $C_{1-4}$-allyl, hydroxy, methoxy, nitro, methylsulfonyl or triflouromethylthio.

3. A compound of the formula I or a pharmaceutically acceptable salt thereof or stereoisomeric forms thereof, (I)

wherein
$R^1$ is hydrogen,
$R^2$ is hydrogen, methyl or ethyl,
$R^3$ is hydrogen, n-butyl, cycloheptyl, 2-fluoroethyl, 3-hydroxypropyl, 3-hydroxy-2,2-dimethylpropyl, 1-(hydroxymethyl)propyl, 3,3,3-trifluoro-2-hydroxypropyl, 3-ethoxypropyl, 2-ethoxy-2-oxoethyl, 3-(dimethylamino)propyl, 6-(hydroxymethyl) cyclohex-3-en-l-yl, 3-hydroxyphenyl, 3-fluorophenyl, 3-(2-pyridin-2-yl-ethyl) phenyl, 3,4-dimethylphenyl, 4-tert-butylphenyl, benzyl, 4-hydroxy-3-methoxybenzyl, 4-methylsulfonylbenzyl, 2-nitrobenzyl,2-chloro-6-fluorobenzyl, 2-[(trifluoromethyl) thio]benzyl, 2-hydroxy-2-phenylethyl, 2-(3,4-dimethoxyphenyl)ethyl, 2-(2-chlorophenyl)ethyl, 2-(4-methylphenyl)ethyl, [4-bromophenyl]amino, or methoxy,
$R^{3a}$ is hydrogen, methyl,
$R^4$ is hydrogen,
$R^5$ is halogen,
$R^6$ is hydrogen, methyl or Cl, and
$R^7$ is hydrogen, methyl, Br, F or Cl.

4. A compound according to claim 1 wherein $R^2$ is hydrogen or methyl.

5. A compound according to claim 1 wherein $R^3$ is hydrogen.

6. A compound according to claim 1 wherein $R^{3a}$ is hydrogen.

7. A compound according to claim 1 wherein $R^6$ is hydrogen.

8. A compound according to claim 1 wherein $R^7$ is hydrogen, Br, or F.

9. A compound according to claim 1 wherein $R^2$ is $C_{1-20}$-alkyl and the carbon atom to which $R^2$ is attached is in the "S"-configuration.

10. A compound selected from
2-(5-iodo-2-oxo-2,3-dihydro-1H-indol-1-yl)acetamide;
2-(5-chloro-2-oxo-2,3-dihydro-1H-indol-1-yl)acetamide;
2-(5,7-dibromo-2-oxo-2,3-dihydro-1H-indol-1-yl)acetamide;
2-(5-chloro-2-oxo-2,3-dihydro-1H-indol-1-yl)propanamide;
(2R)-2-(5-chloro-2-oxo-2,3-dihydro-1H-indol-1-yl)propanamide;
(2S)-2-(5-chloro-2-oxo-2,3-dihydro-1H-indol-1-yl)propanamide;
2-(5-fluoro-2-oxo-2,3-dihydro-1H-indol-1-yl)acetamide;
2-(5-bromo-2-oxo-2,3-dihydro-1H-indol-1-yl)acetamide;
2-(2-oxo-5-(trifluoromethyl)-2,3-dihydro-1H-indol-1-yl)acetamide;
2-(5-chloro-2-oxo-2,3-dihydro-1H-indol-1-yl)butanamide;
(+)-2-(5-chloro-2-oxo-2,3-dihydro-1H-indol-l-yl)butanamide;
(−)-2-(5-chloro-2-oxo-2,3-dihydro-1H-indol-1-yl)butanamide;
2-(5-bromo-2-oxo-2,3-dihydro-1H-indol-1-yl)propanamide;
(−)-2-(5-bromo-2-oxo-2,3dihydro-1H-indol-1-yl )propanamide;
(+)-2-(5-bromo-2-oxo-2,3-dihydro-1H-indol-1-yl )propanamide;
2-(5-chloro-7-fluoro-2-oxo-2,3-dihydro-1H-indol-1-yl)acetamide;
2-(5-chloro-2-oxo-2,3-dihydro-1H-indol-1-yl)-N-(3-hydroxyphenyl)acetamide;
2-(5-chloro-2-oxo-2,3-dihydro-1H-indol-1-yl)-N-(3-fluoroplenyl)acetamide;
2-(5-chloro-2-oxo-2,3-dhydro-1H-indol-1-yl)-N-[6-(hydroxymethyl)cyclohex-3-en-1-yl]acetamide;
2-(5-chloro-2-oxo-2,3-dihydro-1H-indol-1-yl)-N-(4-hydroxy-3-methoxybenzyl )acetamide;
2-(5-chloro2-oxo-2,3-dihydro-1H-indol-1-yl)-N-[4-(methylsulfonyl)benzyl]acetamide;
N'-(4-bromophenyl)-2-(5-chloro-2-oxo-2,3-dihydro-1H-indol-1-yl)acetohydrazide;
N-butyl-2-(5-chloro-2-oxo-2,3-dihydro-1H-indol-1-yl)acetamide;
2-(5-chloro-2-oxo-2,3-dihydro-1H-indol-1-yl)-N-(3-hydroxypropyl)acetamide;
2-(5-chloro-2-oxo-2,3-dihydro-1H-indol-1-yl)-N-[3-(dimethylamino)propyl]acetamide;
ethyl {[(5-chloro-2-oxo-2,3-dihydro-1H-indol-1-yl)acetyl]amino}acetate;
2-(5-chloro-2-oxo-2,3-dihydro-1H-indol-1-yl)-N-(3-ethoxypropyl)acetamide;
2-(5-chloro-2-oxo-2,3-dihydro-1H-indol-1-yl)-N-(2-fluoroethyl)acetamide;
2-(5-chloro-2-oxo-2,3-dihydro-1H-indol-1-yl)-N-methoxy-N-methylacetamide;
2-(5-chloro-2-oxo-2,3-dihydro-1H-indol-1-yl)-N-(3,4-dimethylphenyl)acetamide;
N-(4-tert-butylphenyl)-2-(5-chloro-2-oxo-2,3-dihydro-1H-indol-1-yl) acetamide;
2-(5-chloro-2-oxo-2,3-dihydro-1H-indol-1-yl)-N-(3-hydroxy-2,2-dimethylpropyl)acetamide;
2-(5-chloro-2-oxo-2,3-dihydro-1H-indol-1-yl)-N-[1-(hydroxymethyl)propyl]acetamide;
2-(5-chloro-2-oxo-2,3-dihydro-1H-indol-1-yl)-N-(3,3,3-trifluoro-2-hydroxypropyl)acetamide;
2-(5-chloro-2-oxo-2,3-dihydro-1H-indol-1-yl)-N-(2-hydroxy-2-phenylethyl) acetamide;
2-(5-chloro-2-oxo-2,3-dihydro-1H-indol-1-yl)-N-[2-(3,4-dimethoxyphenyl)ethyl]acetamide;
2-(5-chloro-2-oxo-2,3-dihydro-1H-indol-1-yl)-N-[2-(2-chlorophenylethyl]acetamide;
2-(5-chloro-2-oxo-2,3-dihydro-1H-indol-1-yl)-N-[2-(4-methylphenyl)ethyl]acetamide;
2-(5-chloro-2-oxo-2,3-dihydro-1H-indol-1-yl)-N-[2-(3,4,5,6-tetrahydro-1-benzazocin-1(2H)-yl)propyl]acetamide;
2-(5-chloro-2-oxo-2,3-dihydro-1H-indol-1-yl)-N-(2-nitrobenzyl)acetamide;
N-(2-chloro-6-fluorobenzyl)-2-(5-chloro-2-oxo-2,3-dihydro-1H-indol-1-yl) acetamide;
N-benzyl-2-(5-chloro-2-oxo-2,3-dihydro-1H-indol-1-yl)-N-methylacetamide;
2-(5-chloro-2-oxo-2,3-dihydro-1H-indol-1-yl)-N-{2-[(trifluoromethyl)thio]benzyl}acetamide;
2-(5-chloro-2-oxo-2,3-dihydro-1H-indol-1-yl)-N-cycloheptylacetamide; and
pharmaceutically acceptable salts thereof.

11. A pharmaceutical composition comprising an effective amount of a compound according to claim 1 in combination with a pharmaceutically acceptable diluent or carrier.

* * * * *

UNITED STATES PATENT AND TRADEMARK OFFICE
CERTIFICATE OF CORRECTION

| | | |
|---|---|---|
| PATENT NO. | : 7,645,887 B2 | Page 1 of 1 |
| APPLICATION NO. | : 10/550667 | |
| DATED | : January 12, 2010 | |
| INVENTOR(S) | : Starck et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 438 days.

Signed and Sealed this

Sixteenth Day of November, 2010

David J. Kappos
*Director of the United States Patent and Trademark Office*